(12) United States Patent
Beijnen et al.

(10) Patent No.: US 9,089,544 B2
(45) Date of Patent: Jul. 28, 2015

(54) COMPOSITION

(75) Inventors: Jacob Hendrik Beijnen, Amsterdam (NL); Johannes Henricus Matthias Schellens, Amsterdam (NL); Johannes Jan Moes, Amsterdam (NL); Bastiaan Nuijen, Amsterdam (NL)

(73) Assignees: Slotervaart Participaties BV, Amsterdam (NL); Stichting Het Nederlands Kanker Instituut, Amsterdam (NL)

( * ) Notice: Subject to any disclaimer, the term of this patent is extended or adjusted under 35 U.S.C. 154(b) by 373 days.

(21) Appl. No.: 12/197,432

(22) Filed: Aug. 25, 2008

(65) Prior Publication Data
US 2009/0054503 A1  Feb. 26, 2009

Related U.S. Application Data

(60) Provisional application No. 60/957,764, filed on Aug. 24, 2007.

(51) Int. Cl.
| | | |
|---|---|---|
| *A61K 9/14* | (2006.01) | |
| *A61K 31/337* | (2006.01) | |
| *A61K 9/16* | (2006.01) | |
| *A61K 9/48* | (2006.01) | |
| *A61K 31/427* | (2006.01) | |
| *A61K 9/00* | (2006.01) | |

(52) U.S. Cl.
CPC ............. *A61K 31/337* (2013.01); *A61K 9/1617* (2013.01); *A61K 9/1635* (2013.01); *A61K 9/1694* (2013.01); *A61K 9/4858* (2013.01); *A61K 31/427* (2013.01); *A61K 9/0095* (2013.01)

(58) Field of Classification Search
None
See application file for complete search history.

(56) References Cited

U.S. PATENT DOCUMENTS

| | | | | |
|---|---|---|---|---|
| 6,395,770 | B1 * | 5/2002 | Broder et al. ................. | 514/449 |
| 2002/0041896 | A1 | 4/2002 | Straub et al. | |
| 2002/0082291 | A1 | 6/2002 | Bissery | |
| 2003/0220391 | A1 * | 11/2003 | Bogardus et al. ............ | 514/449 |
| 2004/0052847 | A1 | 3/2004 | Namburi | |
| 2004/0071777 | A1 * | 4/2004 | Trespidi et al. ............... | 424/486 |
| 2004/0167139 | A1 | 8/2004 | Potter | |
| 2006/0078619 | A1 * | 4/2006 | Woo et al. ..................... | 424/489 |
| 2006/0188566 | A1 * | 8/2006 | Liversidge et al. ........... | 424/451 |
| 2011/0207804 | A1 | 8/2011 | Beijnen | |

FOREIGN PATENT DOCUMENTS

| | | |
|---|---|---|
| WO | WO 2004/012714 | 2/2004 |
| WO | WO 2006/026592 | 3/2006 |
| WO | WO 2008/027932 | 3/2008 |
| WO | WO 2008/088776 | 7/2008 |
| WO | WO 2008/118754 | 10/2008 |
| WO | 2010020799 | 2/2010 |

OTHER PUBLICATIONS

Ikezoe "HIV-1 Protease Inhibitor, Ritonavir: A Potent Inhibitor of CYP3A4, Enhanced the Anticancer Effects of Docetaxel in Androgen-Independent Prostate Cancer Cells in vitro and in vivo"; Cancer Research 61, 2001; pp. 7426-7431.*
Bardelmeijer et al., "Low Systemic Exposure of Oral Docetaxel in Mice Resulting From Extensive First-Pass Metabolism is Boosted by Ritonavir," *Cancer Research*, vol. 62, pp. 6158-6164, Nov. 1, 2002.
Bundow and Aboulafia, "Potential Drug Interaction with Paclitaxel and Highly Active Antiretroviral Therapy in Two Patients with AIDS-Associated Kaposi Sarcoma," *American Journal of Clinical Oncology*, vol. 27, No. 1, pp. 81-84, Feb. 2004.
Chen et al., "Preparation, Characterization and in Vitro Evaluation of Solid Dispersions Containing Docetaxel," *Drug Development and Industrial Pharmacy*, vol. 34, pp. 588-594, 2008.
Ikezoe et al., "HIV-1 Protease Inhibitor, Ritonavir: A Potent Inhibitor of CYP3A4, Enhanced the Anticancer Effects of Docetaxel in Androgen-Independent Prostate Cancer Cells in vitro and in vivo," *Cancer Research*, vol. 64, pp. 7426-7431, Oct. 15, 2004.
Kruijtzer et al., "Improvement of Oral Drug Treatment by Temporary Inhibition of Drug Transporter and/or Cytochrome P450 in the Gastrointestinal Tract and Liver: An Overview," *The Oncologist*, vol. 7, pp. 516-530, 2002.
Leuner and Dressman, "Improving drug solubility for oral delivery using solid dispersions," *EP Journal of Pharmaceutics and Biopharmaceutics*, vol. 50, pp. 47-60, 2000.
Junghanns & Mueller, "Nanocrystal technology, drug delivery and clinical applications," *Int. J. Nanomedicine* 3, 295-309, 2008.
Non-final office action for U.S. Appl. No. 13/060,037 mailed Sep. 25, 2012.
Response to non-final office action for U.S. Appl. No. 13/060,037, filed Dec. 21, 2012.
Final office action for U.S. Appl. No. 13/060,037 mailed Mar. 20, 2013.

* cited by examiner

*Primary Examiner* — Susan Tran
(74) *Attorney, Agent, or Firm* — Banner & Witcoff, Ltd.

(57) ABSTRACT

Pharmaceutical compositions and methods for the treatment of neoplastic disease and comprising the combination of a taxane, such as docetaxel, with a CYP3A4 inhibitor, such as ritonavir. Methods of treatment of neoplastic disease incorporating the administration of a taxane and the administration of a CYP3A4 inhibitor, either simultaneously or separately, are also included. Further, kits for carrying out the methods are included. Solid pharmaceutical taxane compositions for oral administration comprising a substantially amorphous taxane, a carrier and a surfactant are also included.

12 Claims, 15 Drawing Sheets

COMPOSITION

The invention relates to pharmaceutical compositions. In particular, though not exclusively, it relates to compositions and methods for the treatment of neoplastic disease.

The administration of drugs in oral form provides a number of advantages. The availability of an oral anticancer drug is important when treatment must be applied chronically to be optimally effective e.g., the 5-fluorouracil (5-FU) prodrugs (e.g. capecitabine) and drugs that interfere with signal transduction pathways or with the angiogenesis process [1]. In addition, oral drugs can be administered on an outpatient basis or at home, increasing convenience and patient quality of life, and possibly decreasing the costs by reducing hospital admissions [2]. Therefore, it is advantageous to try to administer anticancer drugs orally.

In general, the oral administration of drugs is convenient and practical. However, the majority of anticancer drugs unfortunately have a low and variable oral bioavailability [1]. Typical examples are the widely used taxanes, docetaxel and paclitaxel, which have an oral bioavailability of less than 10% [3, 4]. Several other anticancer agents with higher bioavailability demonstrate higher variability. Examples include the topoisomerase I inhibitors, the vinca alkaloids, and mitoxantrone [1, 5, 6]. In view of the narrow therapeutic window, the variable bioavailability may result in unanticipated toxicity or decreased efficacy when therapeutic plasma levels are not achieved. Hellriegel et al. demonstrated in a study that the plasma levels after oral administration are generally more variable than after i.v. administration [7]. Adequate oral bioavailability is important when the period of drug exposure is a major determinant of anticancer therapy [8]. Adequate oral bioavailability is also important to prevent high local drug concentrations in the gastro-intestinal tract that may give local toxicity.

Chen et al. [95] conducted experiments to try to improve the solubility of the anticancer drug docetaxel in order to improve its bioavailability. Chen et al. tried using solid dispersions of docetaxel with various carriers, namely glyceryl monosterate, PVP-K30 or poloxamer 188. Chen et al. found that poloxamer 188 increased the solubility of docetaxel to about 3.3 µg/ml after 20 minutes (in a standard dissolution test) and to a maximum of about 5.5 µg/ml after about 120 minutes when a docetaxel to poloxamer ratio of 5:95 was used. PVP-K30 only increased the solubility of docetaxel to about 0.8 µg/ml after 20 minutes and to a maximum of about 4.2 µg/ml after about 300 minutes. Glycerol monostearate hardly increased the solubility of docetaxel at all. Thus, the solubility and dissolution rate of docetaxel was not increased to a particularly high level.

There are a number of important mechanisms that can explain the variable and/or low oral bioavailability of anticancer drugs, such as high affinity for drug transporters in the gastrointestinal tract, which limits absorption, and high extraction of the drug by extensive metabolism in the intestine and/or liver (first-pass effect) [1, 4, 9]. Other important factors include structural instability and limited solubility of the drug in the gastrointestinal fluids, drug-drug and drug-food interactions, motility disorders, obstructive disorders, existence of nausea and vomiting or local toxicity in the gastrointestinal tract.

With regard to the drug transporters and metabolic enzymes that affect the bioavailability of oral drugs, it has been speculated that the main drug transporter and metabolic enzymes responsible for the low/variable oral bioavailability of anticancer drugs are P-glycoprotein (P-gp) and cytochrome P450 (CYP) isoenzymes.

P-glycoprotein (P-gp) is a membrane-bound multidrug transporter which functions as an energy-dependent transport or efflux pump to decrease intracellular accumulation of drugs by exporting xenobiotics from the cell. P-gp has been identified in normal tissues with an excretory function such as the biliary canalicular membrane of hepatocytes, the luminal membrane of endothelial cells in the blood-brain barrier and blood-testis barrier, the apical membrane of the syncytial trophoblasts of the placenta, the epithelial apical membrane of the intestine, and the renal proximal tubules. P-gp may possess an important barrier function in protecting tissues against xenotoxins [9-12].

It is believed that P-gp prevents certain pharmaceutical compounds from transversing the mucosal cells of the small intestine and, therefore, from being absorbed into the systemic circulation. A wide range of drugs with varying physicochemical characteristics and pharmacological activity, such as verapamil, quinidine, and cyclosporin A (CsA) and the new active blockers GF120918 (elacridar), LY335979 (zosuquidar), and R101933 have been shown in clinical studies to modulate P-gp [13-18]. Mechanisms by which P-gp modulators can influence the pharmacokinetics of the anticancer drug after i.v. administration are competition for cytochrome P450 (CYP)-mediated intestinal or liver metabolism, inhibition of P-gp-mediated biliary excretion, intestinal transport, and inhibition of renal elimination [19, 20]. Only a few prospective randomized studies combining an anticancer agent with or without a modulator have been performed. These studies revealed that dose reductions of the anticancer drug, when combined with a modulator, were necessary to prevent severe drug-related toxicity. In addition, these studies did not show any survival benefit for the combination of an anticancer drug with a modulator [21-23].

For many anticancer drugs, cytochrome P450 (CYP) is the main oxidative drug metabolizing enzyme system. CYP isoenzymes are highly expressed in the liver and intestines, but the exact contribution of each isoenzyme in the metabolism of drugs is unknown. It is recognised that intestinal extraction by this enzyme system plays an important role in limiting oral bioavailability of drugs [31]. Humans have four identified functional CYP3A enzymes which are the predominant drug metabolizing enzymes and account for approximately 30% of hepatic CYP and more than 70% of intestinal CYP expression [24, 30, 32, 33].

Some P-gp modulators also appear to be substrates for CYP3A, an isoenzyme of the CYP system. The overlap in substrate selectivity for P-gp and CYP3A, combined with their tissue localization, suggests that these two proteins cooperate and constitute an absorption barrier against toxic xenobiotics [24-26]. Cummins et al. have confirmed this and showed that P-gp can affect intestinal drug metabolism (especially the isoenzyme CYP3A4) by controlling the access of a drug to the intracellular metabolizing enzyme system [27]. Therefore, it appears that CYP3A and P-gp may play a role in limited and/or variable oral bioavailability of shared substrate drugs in the intestines.

The taxanes, paclitaxel and docetaxel, have proven anticancer activity in several tumour types (e.g., breast, ovarian, head and neck cancer, and non-small cell lung cancer [NSCLC]). Currently, the drugs are administered intravenously at different dosages and schedules [34]. However, in oral formulations, the taxanes have very low bioavailability. This is speculated to be due to the action of P-gp and CYP3A. Studies attempting to increase the bioavailability of orally administered drugs have been performed in mice and humans with several anticancer drugs (e.g., the taxanes).

When paclitaxel is administered orally, the bioavailability is very low (<10%). This is caused by the high affinity of paclitaxel for P-gp, which is present in the gastrointestinal tract [4, 10, 35, 36]. In addition, presystemic elimination in the intestinal wall and liver by the CYP isoenzymes 3A4 and 2C8 may also play a role in the low oral bioavailability of paclitaxel [37-39]. Recent studies with wild-type mice and mdr1a P-gp knockout mice have shown unambiguously that P-gp limits the absorption of paclitaxel. In a proof-of-concept study in knockout mice compared with wild-type mice, the investigators demonstrated a sixfold and a twofold increase of the area under the plasma concentration-time curve (AUC) of paclitaxel after oral and i.v. administration, respectively [4]. The fraction of unchanged paclitaxel recovered from the faeces of wild-type mice after oral administration was 87% of the dose compared with 3% in mdr1a P-gp knockout mice. Despite the complete absorption from the gastrointestinal tract, the bioavailability did not increase to 100%, probably due to first-pass intestinal/hepatic extraction [4, 40].

Based on this observation, several new studies have been initiated with P-gp inhibitors in combination with paclitaxel in order to enhance the oral bioavailability. Studies in mice revealed that coadministration of SDZ PSC833, a cyclosporin D analogue and potent P-gp inhibitor, with paclitaxel resulted in a 10-fold increase in systemic exposure [41]. A similar study was performed with CsA and paclitaxel that has shown comparable effects [42]. The oral bioavailability in wild-type mice increased from 9% to 67% when CsA was coadministered. It was also noted that the plasma levels of paclitaxel obtained in wild-type mice cotreated with CsA were even higher than those obtained in knockout mice that were treated with oral paclitaxel without CsA. This can be explained by increased uptake by inhibition of P-gp in the gastrointestinal tract and decreased elimination by inhibition of CYP3A [42-45]. However, blockade of other yet unidentified drug transporters or drug eliminating pathways cannot be ruled out.

The use of CsA for long-term oral dosing has been associated with immunosuppressive effects which are detrimental to the health of the subject. Therefore, an alternative, non-immunosuppressive P-gp blocker, GF120918, was explored to enhance the oral bioavailability of paclitaxel. GF120918 was primarily developed to reverse P-gp-mediated multidrug resistance in tumours [16]. In a recently published study, Bardelmeijer et al. demonstrated that GF120918 significantly increased the oral bioavailability of paclitaxel [46]. The oral bioavailability of paclitaxel in wild-type mice increased from 8.5% to 40% and the pharmacokinetics of paclitaxel in wild type mice receiving GF120918 were similar to that found in mdr1a/b P-gp knockout mice. Thus, GF120918 effectively blocks P-gp in the intestines and most likely does not interfere with other pathways involved in paclitaxel uptake or elimination. Of note, it was recently demonstrated that GF120918 is also an effective inhibitor of the ABC drug transporter BCRP (ABCG2) [28, 29].

Docetaxel is also a substrate of P-gp, first shown in 1994 by Wils et al. [47, 48]. Because of the encouraging results obtained with paclitaxel in combination with P-gp inhibitors, studies in mice were also performed with docetaxel. These studies confirmed that P-gp also plays an important role in the low bioavailability of docetaxel. The AUC of oral docetaxel increased ninefold by coadministration with CsA [49]. In addition, coadministration of ritonavir, an inhibitor of CYP3A4 with minor P-gp inhibiting properties, was tested in mice. CYP3A4 is the major enzyme responsible for metabolic breakdown of docetaxel in humans [50]. The inventors executed preclinical studies in mice in which ritonavir was coadministered with docetaxel and showed an increase in the apparent bioavailability from 4% to 183%. Extensive first-pass metabolism might also largely contribute to the low bioavailability of oral docetaxel in mice [49]. Cytochrome P450 enzymes in the intestines of mice (referred to as Cyp) are different from those found in humans and have different substrate specificities. Further, regulation of expression of CYPs between mice and humans differs considerably due to differences in the activity, expression and regulation of transcription factors, for example, PXR for human CYP3A [88-92]. Therefore, these studies in mice cannot be relied upon to give any indication of the results in humans since the physiology, enzymes, etc. of mice are completely different to humans. Accordingly, mouse data cannot simply be extrapolated to humans. Further, this study in mice used an extremely high dose of docetaxel (10-30 mg/kg) which would be lethal in human subjects, and also a high dose of ritonavir (12.5 mg/kg). For a 72 kg individual this would mean 720-2160 mg of docetaxel. Patients are, however, now usually treated in the clinic with docetaxel dosages between 100 and 200 mg (intravenously). Clearly, due to the high level of drugs that were administered, this approach is not possible in humans. In addition, the mouse data do not provide any evidence about the safety of the oral approach with this combination in humans.

Based on the extensive preclinical results in mice, several clinical proof-of-concept studies were initiated. Patients with solid tumours received one course of 60 mg/m$^2$ oral paclitaxel as a single agent, or 60 mg/m$^2$ oral paclitaxel in combination with 15 mg/kg CsA. Coadministration of oral CsA resulted in an eightfold increase in the systemic exposure to oral paclitaxel, and the apparent bioavailability of oral paclitaxel in this study rose from 4% without CsA to 47% with CsA [3]. This increase in systemic exposure was most likely caused by inhibition of P-gp in the gastrointestinal tract, but inhibition of paclitaxel metabolism also may have contributed to the effect, as was concluded from the preclinical studies [41, 42]. In order to further increase the systemic exposure of paclitaxel, a dose escalation study with oral paclitaxel in combination with CsA revealed that the maximum tolerated dose was 300 mg/m$^2$ and the increase in AUC at the higher doses was not proportional with dose [52]. At this highest dose level, a mass balance study was performed to measure faecal excretion. At the highest dose level of 300 mg/m$^2$, the total faecal excretion was 76%, 61% of which was the parent drug, which can be explained by incomplete absorption of orally administered paclitaxel from the gastrointestinal tract [53]. It was speculated that the high amount of the cosolvent Cremophor EL in the paclitaxel i.v. formulations used for oral administration prevented complete absorption of orally applied paclitaxel. In addition, Cremophor EL, which is responsible for the nonlinear pharmacokinetics of i.v. paclitaxel and for the severe hypersensitivity reactions, was not absorbed following oral administration of paclitaxel, as plasma levels of Cremophor EL were not detected [54-56]. This may be an additional advantage of oral paclitaxel administration [51, 52]. Subsequently, in order to increase the duration of systemic exposure of oral paclitaxel above a threshold level of 0.1 µM, a twice daily (b.i.d.) dose regimen of oral paclitaxel in combination with CsA was explored in patients. At the dose level of 2×90 mg/m$^2$, adequately long systemic exposure of paclitaxel above the level of 0.1 µM was reached with a good safety profile [57]. In these studies the patients ingested orally the intravenous paclitaxel formulation (also containing Cremophor EL and ethanol) [57]. Additionally, a dose-finding study of oral paclitaxel with CsA showed that P-gp inhibition by CsA was maximal at a single dose of 10 mg/kg [58].

In another phase I study, patients received 1,000 mg GF120918 1 hour prior to oral paclitaxel [59]. The increase in systemic exposure to paclitaxel was of the same magnitude as in combination with CsA. Based on the results of these phase I studies, phase II studies were initiated to investigate whether repeated oral administration of paclitaxel was feasible and active. Oral paclitaxel was given b.i.d. once a week in several tumour types: as first- and second-line treatment in NSCLC [60], as first-line treatment in advanced gastric cancer [99], and as second-line treatment in advanced breast cancer [100]. All patients were treated with weekly oral paclitaxel b.i.d. in a dose of 90 mg/m$^2$. CsA, in a dose of 10 mg/kg, was given 30 minutes prior to every paclitaxel dose. In the patients with advanced NSCLC, the overall response rate (ORR) was 26% in 23 evaluable patients [60]. This is comparable with the earlier studies, as were the median time to progression of 3.5 months and median overall survival of 6 months. These studies, in which several single agents such as vinorelbine, gemcitabine, and the taxanes were used, revealed response rates between 8%-40% and median overall survival ranged from 6-11 months [61-66].

In advanced gastric cancer, chemotherapy is given with palliative intent. Combination chemotherapy with agents such as 5-FU/doxorubicin combined with mitomycin or methotrexate, or the epirubicin/cisplatin/5-FU regimen are schedules that are frequently used and have shown response rates between 20%-50% [67-70]. Paclitaxel has also shown anti-tumour activity in patients with advanced gastric cancer (ORR: 5%-23%) in first- and in second-line treatment [71-73]. The ORR in this study was 32% in 24 evaluable patients. The toxicity profile of this b.i.d. weekly schedule is well manageable [99]. The most prevalent toxicity in the group of patients with NSCLC was grade 3/4 neutropenia, which was observed in 54% of patients. This is comparable with the standard every-3-week i.v. paclitaxel schedule [65, 66].

The prevalence of neurotoxicity was lower compared with the every-3-week schedule, which may be explained by the lower peak plasma concentrations of paclitaxel in this study. This was also observed in patients who received the 24-hour infusion versus the 3-hour infusion of paclitaxel [74], although it can be questioned whether paclitaxel plasma levels after i.v. administration (thus in the presence of Cremophor EL) can be compared with those after oral paclitaxel (thus without Cremophor EL).

For docetaxel, a similar clinical proof-of-concept study was carried out in patients with solid tumours. Patients received one course of oral docetaxel 75 mg/m$^2$ with or without a single oral dose of CsA 15 mg/kg. Pharmacokinetic results showed that coadministration of oral CsA resulted in a 7.3-fold increase of the systemic exposure of docetaxel. The apparent bioavailability of oral docetaxel increased from 8% without CsA to 90% with CsA [75]. This increase in systemic exposure can be explained by inhibition of CYP3A4, as well as by P-gp inhibition in the gastrointestinal tract by CsA, but the magnitude of both mechanisms cannot be determined exactly. The effect of CsA on the bioavailability of docetaxel was less pronounced in mice [49] compared with humans [75], but the reasons for this modest effect in mice are not clear. A phase II study in advanced breast cancer with weekly oral docetaxel plus CsA was also performed. This schedule was given weekly for 6 weeks followed by a 2-week rest. A weekly oral dose of 100 mg docetaxel was given, leading to an AUC equivalent to a weekly i.v. dose of 40 mg/m$^2$, which was reasonably well tolerated [76]. CsA was given 30 minutes prior to the intake of oral docetaxel in a dose of 15 mg/kg. The i.v. formulation of docetaxel was used as a drinking solution. In 25 patients evaluable for response, an ORR of 52% was noted.

The most frequently recorded toxicities were neutropenia, diarrhoea, nail toxicity, and fatigue. However, haematological toxicity seems to be less severe than after i.v. administration [77]. The response rate in this study is in the upper range of results described in the literature [76-79].

The inter- and intra-patient variabilities in the AUC of docetaxel after oral administration were in the same range as observed after i.v. administration of docetaxel (29%-53%) [80, 81].

The weekly or b.i.d. administration of an oral dose of CsA, in combination with oral docetaxel or paclitaxel, could result in renal toxicity or infections due to immunosuppression [82]. Therefore, an alternative drug to improve the clinical bioavailability of oral docetaxel or paclitaxel would, in the present inventors view, be preferred.

Intensive weekly oral schedules with taxanes are feasible and show clinically meaningful activity in advanced breast, gastric, and NSCLC. The oral schedule is convenient and has a favourable haematological toxicity profile, and the non-haematological toxicity is acceptable.

The prior art appears to be primarily focused on inhibiting the action of P-gp in order to improve the bioavailability and pharmacokinetic properties of anticancer drugs. This has been done using various drugs, for example, CsA and GF120918. It appears that P-gp was seen as the most important protein to block in order to improve bioavailability of oral drugs.

Accordingly, in a first aspect, the present invention provides a pharmaceutical composition for oral administration comprising a taxane and a CYP3A4 inhibitor, such as ritonavir, together with one or more pharmaceutically acceptable excipients.

The advantage of using ritonavir in combination with a taxane is that the oral bioavailability of the taxane is increased so that more drug is absorbed from the intestines into the blood stream. This is due to the inhibition of CYP3A4 which stops the drug from being metabolised and the minor P-gp inhibiting properties. The ritonavir also reduces the elimination of the taxane from the body by inhibiting CYP3A4 metabolism in the liver. This means that a higher blood plasma level of the taxane is reached for a longer period of time. For example, docetaxel metabolites are less pharmacologically active than docetaxel itself. Therefore, by inhibiting metabolism of docetaxel, the most pharmacologically active form is present in the bloodstream at a higher level and also for longer. This provides a greater therapeutic effect. As a result, it may be possible to reduce the amount of taxane per dose. Further, inhibition of CYP3A4 reduces interpatient variability in bioavailability and elimination due to differing levels of CYP activity in different patients.

The targeting and inhibition of CYP3A4 with ritonavir rather than targeting P-gp improves the bioavailability of oral taxanes by stopping their metabolism. This, on the whole, is a different approach to that followed by the prior art.

Pharmaceutical compositions of this invention comprise any taxane, or pharmaceutically acceptable salts and esters thereof, and ritonavir (or pharmaceutically acceptable salts and esters thereof) together with any pharmaceutically acceptable carrier, adjuvant or vehicle. Pharmaceutically acceptable carriers, adjuvants and vehicles that may be used in the pharmaceutical compositions of this invention include, but are not limited to, ion exchangers, alumina, aluminium stearate, lecithin, serum proteins, such as human serum albumin, buffer substances such as phosphates, glycerine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. The pharmaceutical compositions of this invention may contain any conventional non-toxic pharmaceutically-acceptable carriers, adjuvants or vehicles.

The pharmaceutical compositions of this invention may be orally administered in any orally acceptable dosage form including, but not limited to, capsules, tablets, a powder or coated granules. Suspensions, solutions and emulsions, preferably in an aqueous vehicle, may also be employed. Tablets may be formulated to be immediate release, extended release, repeated release or sustained release. They may also, or alternatively, be effervescent, dual-layer and/or coated tablets. The extended release, repeated release and sustained release formulations can be for one or both active ingredients. Tablets can be formed from solid dispersions or solid solutions of the taxane and/or ritonavir. Capsules may be formulated to be immediate release, extended release, repeated release or sustained release. They may be solid-filled or liquid-filled capsules. The extended release, repeated release and sustained release formulations can be for one or both active ingredients. Capsules can be formed from solid dispersions or solid solutions of the taxane and/or ritonavir or the taxane and/or ritonavir can be dissolved or dispersed in a liquid. For example, a possible solvent for liquid filled capsules is triacetin. This appears to be a particularly good solvent for paclitaxel. Aqueous solutions can be "ready to use", prepared from a powder or powders, prepared from a solid dispersion or dispersions or by mixing solutions of the taxane and ritonavir. The aqueous solutions may also comprise other pharmaceutical excipients, for example, polysorbate 80 and ethanol. In the case of tablets and capsules for oral use, carriers which are commonly used include sucrose, cyclodextrins, polyethyleneglycols, polymethacrylates, polyoxyethylene sorbitan fatty acid esters, polyoxyethylene stearates, mannitol, inulin, sugars (dextrose, galactose, sucrose, fructose or lactose), HPMC (hydroxypropylmethyl cellulose), PVP (polyvinyl pyrrolidone) and corn starch. Lubricating agents, such as magnesium stearate, are also typically added. For oral administration in a capsule form, useful diluents include lactose and dried corn starch. For tablets and capsules, other pharmaceutical excipients that can be added are binders, fillers, filler/binders, adsorbents, moistening agents, disintegrants, lubricants, glidants, surfactants and the like. Tablets and capsules may be coated to alter the appearance or properties of the tablets and capsules, for example, to alter the taste or to colour coat the tablet or capsule. When aqueous suspensions are administered orally, the active ingredient is combined with emulsifying and suspending agents. If desired, certain sweetening and/or flavouring and/or colouring agents may be added.

Solid dispersions or solid solutions of the taxane and ritonavir can be formed using any suitable method and may include carriers, for example, polymers. Such methods are well known to those skilled in the art [93, 94]. The taxane and the ritonavir in the solid dispersion can be in an amorphous, crystalline or partly amorphous/partly crystalline state. Often, organic solvents are used in the preparation of solid dispersions. These can be any suitable organic solvent, for example, TBA (tertiary butyl alcohol), ethanol, methanol, DMSO (dimethyl sulfoxide) and IPA (iso-propyl alcohol).

Any methods for removing organic and/or aqueous solvents from solid dispersion solutions can be used, for example, freeze drying, spray drying, spray-freeze drying and vacuum drying.

In compositions, particularly solid compositions, for oral administration, the taxane and ritonavir may be present in the same dosage form, or may be present in separate dosage forms. If present in the same dosage form, the taxane and ritonavir may be formulated together, or may be present in separate compartments of a multi-compartment dosage form, such as a multi-layer tablet, or a compartmentalised capsule.

For the compositions comprising modified release formulations, for example, extended release, repeated release and sustained release formulations, the aim is to maintain adequate blood levels of one or both active ingredients for a prolonged period of time after administration.

A repeated release formulation, e.g. a tablet or capsule, is one which is capable of releasing an adequate dose of taxane (e.g. docetaxel) and ritonavir immediately (e.g. at time t=0 h) and releasing an additional booster dose of ritonavir later on (e.g. at time t=4 h when the Cmax of ritonavir is typically reached). This can be achieved, for example, by separating the initial doses of docetaxel and ritonavir from the booster dose of ritonavir by an enteric coating or a polymeric coating containing enzymatically cleavable bonds which enable the coating to be broken down and dissolved in the intestines. Alternatively, this may be achieved by filling a capsule with coated and uncoated granules, wherein the coated granules contain only ritonavir and the uncoated granules contain docetaxel and ritonavir. This could, of course, also be achieved by combining an immediate release docetaxel tablet/capsule with a repeated release tablet/capsule of ritonavir. Any suitable enteric coating can be used, for example, cellulose acetate phthalate, polyvinyl acetate phthalate and suitable acrylic derivates, e.g. polymethacrylates.

In one embodiment, a second booster dose (thus a total of three doses) of ritonavir could be delivered by the same principle, i.e. repeated release, some hours after the first booster dose (e.g. when the Cmax of the first booster dose of ritonavir is reached).

A sustained release formulation is one which is capable of, for example, releasing an adequate dose of taxane and an initial priming/loading dose of ritonavir followed by the slow release of a maintenance dose of ritonavir. For example, this could be achieved by a single oral dosage form of docetaxel and ritonavir or by combining an immediate release tablet/capsule of docetaxel with a sustained release tablet/capsule of ritonavir.

Modified release formulations can, for example, utilise inert insoluble matrices, hydrophilic matrices, ion-exchange resins, osmotically controlled formulations and reservoir systems. A typical modified release system could, for example, consist of the following substances: active drug(s), release controlling agent(s) (e.g. matrix formers, membrane formers), matrix or membrane modifiers, solubiliser, pH modifier, lubricant and flow aid, supplementary coatings and density modifiers [84]. Suitable inert excipients include dibasic calcium phosphate, ethyl cellulose, methacrylate copolymer polyamide, polyethylene, polyvinyl acetate. Suitable lipid excipients include carnauba wax, acetyl alcohol, hydrogenated vegetable oils, microcrystalline waxes, mono- and triglycerides, PEG monostearate and PEG. Suitable hydrophilic excipients include alginates, carbopol, gelatin, hydroxypropylcellulose, hydroxypropyl methylcellulose and methylcellulose [84].

In one embodiment of the invention, the composition comprising a taxane and ritonavir may be formulated so that the ritonavir is released slightly earlier or faster than the taxane. This will have the effect of inhibiting the CYP3A4 enzymes in the intestines before a substantial amount of the taxane has been released from the composition. Therefore, this will reduce the amount of the taxane that is broken down by the CYP3A4 enzymes before it reaches the bloodstream and, by virtue of the effect of ritonavir on CYP3A4 in the liver, will also have the effect of reducing the metabolism and elimination of taxane reaching the bloodstream during the early stages of absorption thereof. This effect is demonstrated by FIG. 1 which shows a trend that administration of the ritonavir 60 mins before the docetaxel increases the oral bioavailability and AUC. Although this result is not statistically significant in Example 2, this trend can be seen.

Taxanes are diterpene compounds which originate from plants of the genus *Taxus* (yews). However, some taxanes have now been produced synthetically. Taxanes inhibit cell growth by stopping cell division and are used in treatment of cancer. They stop cell division by disrupting microtubule formation. They may also act as angiogenesis inhibitors. The term "taxane", as used herein, includes all diterpene taxanes, whether produced naturally or artificially, functional derivatives and pharmaceutically acceptable salts or esters which bind to tubulin and/or are substrates for CYP3A4. Preferred taxanes are docetaxel, paclitaxel, BMS-275183, functional derivatives thereof and pharmaceutically acceptable salts or esters thereof. BMS-275183 is a C-3'-t-butyl-3'-N-t-butyloxycarbonyl analogue of paclitaxel [83]. The most preferred taxane is docetaxel, a functional derivative thereof or a pharmaceutically acceptable salt or ester thereof and, in particular, those derivatives which are substrates for CYP3A4.

Derivatives of taxanes containing groups to modify physiochemical properties are also included within the present invention. Thus, polyalkylene glycol (such as polyethylene glycol) or saccharide conjugates of taxanes, with improved or modified solubility characteristics, are included.

The pharmaceutical composition of the present invention can comprise any suitable amount of each of the taxane and ritonavir. Preferably, the composition comprises between about 0.1 mg and about 1000 mg of the taxane. Preferably, the composition also comprises between about 0.1 mg and about 1200 mg of ritonavir. The amounts of each of the taxane and ritonavir will depend on the intended frequency of administration of the composition. For example, the composition can be for administration on a tri-daily, bi-daily or daily basis, every two days, weekly, every two weeks, every three weeks or any other suitable dosing interval. Combinations of these dosage regimens can also be used, for example, the composition can be for bi-daily administration once every week or every two or three weeks. For example, paclitaxel or docetaxel can be administered on a bi-daily basis once a week. The normal weekly dose is split so that a subject takes, for example, half a dose in the morning and the other half in the evening once a week. This has the effect of decreasing the peak levels of the drug in plasma which can help to reduce side effects. It also increases the overall time of systemic exposure of the drug.

If the composition is for daily administration, the composition preferably comprises between about 0.1 mg and about 100 mg of the taxane, more preferably, between about 5 mg and about 40 mg of the taxane, more preferably, between about 5 mg and about 30 mg of the taxane, more preferably, between about 10 mg and about 20 mg of the taxane, and most preferably, about 15 mg of the taxane. Preferably, the composition also comprises between about 50 mg and about 1200 mg of ritonavir, more preferably, between about 50 mg and about 500 mg of ritonavir, more preferably, between about 50 mg and about 200 mg of ritonavir, and most preferably, about 100 mg of ritonavir.

If the composition is for weekly administration, the composition preferably comprises between about 30 mg and about 500 mg of the taxane, more preferably, between about 50 mg and about 200 mg of the taxane and, most preferably, about 100 mg of the taxane. Preferably, the composition also comprises between about 50 mg and about 1200 mg of ritonavir, more preferably, between about 50 mg and about 500 mg of ritonavir, more preferably, between about 50 mg and about 200 mg of ritonavir, and most preferably, about 100 mg of ritonavir.

Surprisingly, it has been found that using ritonavir at a low dose, for example, 100 mg, still has the desired properties of enhancing the bioavailability of taxanes to give an enhanced therapeutic effect. This means that a small dose of ritonavir can be used to have the desired effect, whilst minimising the risk of side effects.

The present invention also provides a composition comprising a taxane and a CYP3A4 inhibitor, such as ritonavir, for use in therapy.

Furthermore, the present invention also provides a composition comprising a taxane and a CYP3A4 inhibitor, such as ritonavir for use in the treatment of neoplastic disease.

The neoplastic disease treated by the present invention is preferably a solid tumour. The solid tumour is preferably selected from breast, lung, gastric, colorectal, head & neck, oesophageal, liver, renal, pancreatic, bladder, prostate, testicular, cervical, endometrial, ovarian cancer and non-Hodgkin's lymphoma (NHL). The solid tumour is more preferably selected from breast, gastric, ovarian, prostate, head & neck and non-small cell lung cancer.

In one embodiment, the treatment of the neoplastic disease comprises administration of the composition and subsequently, after a predetermined period of time, administration of a booster dose of ritonavir. The booster dose is preferably administered between about 0 hours and about 12 hours after the composition, more preferably, between about 1 hour and about 10 hours after the composition, more preferably, between about 2 hours and about 8 hours after the composition, more preferably, between about 3 hours and about 5 hours after the composition and, most preferably, about 4 hours after the composition. The booster dose is preferably between about 50 mg and about 1200 mg of ritonavir, more preferably, between about 50 mg and about 500 mg of ritonavir, more preferably, between about 50 mg and about 200 mg of ritonavir, and most preferably, about 100 mg of ritonavir.

Surprisingly, the administration of a booster dose of ritonavir has been found to provide a therapeutic level of the taxane in the bloodstream for a longer period of time thereby having a greater therapeutic effect.

In a related aspect, the present invention also provides a method of treatment of a neoplastic disease comprising the administration, to a subject in need of such treatment, of an effective amount of a taxane and a CYP3A4 inhibitor, such as ritonavir.

As with the composition above, the taxane can be any suitable taxane. Preferably, the taxane is selected from docetaxel, paclitaxel, BMS-275183, functional derivatives thereof and pharmaceutically acceptable salts or esters thereof and, more preferably, the taxane is docetaxel, a functional derivative thereof or a pharmaceutically acceptable salt or ester thereof.

When the taxane and the ritonavir are being administered to the subject, they can be administered substantially simultaneously with each other. Alternatively, they can be administered separately from each other. When they are administered separately, the ritonavir is preferably administered before the taxane and, more preferably, approximately 60 minutes before the taxane.

"Substantially simultaneously", as used herein, means administration of the taxane or ritonavir within approximately 20 minutes, more preferably within 15 minutes, more preferably within 10 minutes, even more preferably within 5 minutes, most preferably within 2 minutes of the ritonavir or taxane. Generally, the ritonavir should be administered simultaneously with or before the taxane. The ritonavir and taxane may, in some embodiments, be administered simultaneously, i.e. together in one formulation or simultaneously in two separate formulations.

Any suitable amount of the taxane or ritonavir can be administered in accordance with the method. The dose of taxane and/or ritonavir can be administered in a flat dose (i.e. the same for all patients regardless of weight or body surface area) or a weight-based or body surface area-based dose. Preferably, the taxane and/or ritonavir is administered in a flat dose. Preferably, between about 0.1 mg and about 1000 mg of the taxane is administered. Preferably, between about 0.1 mg and about 1200 mg of ritonavir is administered. The amounts of each of the taxane and ritonavir administered will depend on the intended frequency of administration of the taxane and ritonavir. For example, administration can be on a tri-daily, bi-daily or daily basis, every two days, weekly, every two weeks, every three weeks or any other suitable dosing interval. Combinations of these dosage regimens can also be used, for example, a bi-daily administration once every week or every two or three weeks.

If the method involves daily administration of the taxane and ritonavir, preferably between about 0.1 mg and about 100 mg of the taxane is administered, more preferably, between about 5 mg and about 40 mg of the taxane is administered, more preferably, between about 5 mg and about 30 mg of the taxane is administered, more preferably, between about 10 mg and about 20 mg of the taxane is administered, and most preferably, about 15 mg of the taxane. Preferably, between about 50 mg and about 1200 mg of ritonavir is also administered, more preferably, between about 50 mg and about 500 mg of ritonavir is administered, more preferably, between about 50 mg and about 200 mg of ritonavir is administered and, most preferably, about 100 mg of ritonavir is administered.

If the method involves weekly administration of the taxane and ritonavir, preferably between about 30 mg and about 500 mg of the taxane is administered, more preferably, between about 50 mg and about 200 mg of the taxane is administered and, most preferably, about 100 mg of the taxane is administered. Preferably, between about 50 mg and about 1200 mg of ritonavir is also administered, more preferably, between about 50 mg and about 500 mg of ritonavir is administered, more preferably, between about 50 mg and about 200 mg of ritonavir is administered and, most preferably, about 100 mg of ritonavir is administered.

The method can be for treating any neoplastic disease. Preferably, the neoplastic disease is a solid tumour. Preferably, the solid tumour is selected from breast, lung, gastric, colorectal, head & neck, oesophageal, liver, renal, pancreatic, bladder, prostate, testicular, cervical, endometrial, ovarian cancer and NHL. More preferably, the solid tumour is selected from breast, ovarian, prostate, gastric, head & neck and non-small cell lung cancer.

Preferably, the method is used to treat a human subject.

In one embodiment, the method further comprises the administration of a booster dose of a CYP3A4 inhibitor, such as ritonavir a predetermined period of time after the administration of the first dose of ritonavir (i.e. the dose of ritonavir combined with the dose of the taxane). The booster dose is preferably administered between about 0 hours and about 12 hours after the composition, more preferably, between about 1 hour and about 10 hours after the composition, more preferably, between about 2 hours and about 8 hours after the composition, more preferably, between about 3 hours and about 5 hours after the composition and, most preferably, about 4 hours after the composition. The booster dose is preferably between about 50 mg and about 1200 mg of ritonavir, more preferably, between about 50 mg and about 500 mg of ritonavir, more preferably, between about 50 mg and about 200 mg of ritonavir, and most preferably, about 100 mg of ritonavir.

The present invention also provides a method of treatment of a neoplastic disease, the method comprising administering a composition comprising a taxane, and one or more pharmaceutically acceptable excipients, to a subject receiving a CYP3A4 inhibitor, such as ritonavir simultaneously, separately or sequentially with the taxane.

The present invention further provides a method of treatment of a neoplastic disease, the method comprising administering a composition comprising a CYP3A4 inhibitor, such as ritonavir, and one or more pharmaceutically acceptable excipients, to a subject receiving a taxane simultaneously, separately or sequentially with the CYP3A4 inhibitor, such as ritonavir.

Additionally, the present invention provides a kit comprising a first pharmaceutical composition comprising a taxane and a second pharmaceutical composition comprising a CYP3A4 inhibitor, such as ritonavir, the first and second pharmaceutical compositions being suitable for simultaneous, separate or sequential administration for the treatment of neoplastic disease.

In one embodiment, the kit may further comprise a third pharmaceutical composition comprising a CYP3A4 inhibitor, such as ritonavir being suitable for administration subsequent to the second pharmaceutical composition comprising a CYP3A4 inhibitor, such as ritonavir. It will be appreciated that the second and third pharmaceutical compositions in the kit, each comprising a CYP3A4 inhibitor, such as ritonavir, may be unit dose forms of substantially the same composition.

Alternatively, the kit may comprise a first pharmaceutical composition comprising a taxane and a CYP3A4 inhibitor, such as ritonavir, for the treatment of neoplastic disease. In this case, the kit may further comprise a second pharmaceutical composition comprising a CYP3A4 inhibitor, such as ritonavir being suitable for administration subsequent to the first pharmaceutical composition.

Further, the present invention provides a composition comprising a taxane, and one or more pharmaceutically acceptable excipients, for use in the treatment of neoplastic disease in a subject receiving a CYP3A4 inhibitor, such as ritonavir simultaneously, separately or sequentially with the taxane.

Further still, the present invention provides a composition comprising a CYP3A4 inhibitor, such as ritonavir, and one or more pharmaceutically acceptable excipients, for use in the treatment of neoplastic disease in a subject receiving taxane simultaneously, separately or sequentially with the CYP3A4 inhibitor, such as ritonavir.

It will be appreciated by one skilled in the art that any or all of the preferred features described above in relation to compositions, methods or kits employing ritonavir are equally applicable to those employing other CYP3A4 inhibitors, for example, grapefruit juice or St. John's wort (or components of either), lopinavir or imidazole compounds, such as ketoconazole.

Another problem associated with the prior art is that it has not been possible to develop an oral composition comprising a taxane in which the taxane has a high bioavailability with low variability. Clinical studies with oral paclitaxel [e.g 3] and oral docetaxel [e.g. 75] have been executed where the i.v. taxane formulations (also containing excipients such as Cremophor EL and ethanol, or polysorbate 80 and ethanol) were ingested orally. Nausea, vomiting and an unpleasant taste are frequently reported by the patients.

As discussed earlier, Chen et al. [95] tried using a solid dispersion of docetaxel in combination with poloxamer 188 or PVP-K30 to improve the solubility and dissolution rate of docetaxel. Poloxamer increased the solubility of docetaxel to about 3.3 µg/ml after 20 minutes and to a maximum of about 5.5 µg/ml after about 120 minutes when a docetaxel to poloxamer ratio of 5:95 was used (see FIG. 7 in Chen paper). PVP-K30 increased the solubility of docetaxel to about 0.8 µg/ml after 20 minutes and to a maximum of about 4.2 µg/ml after about 300 minutes (see FIG. 2). In order to achieve good oral bioavailability, a drug must have a relatively high solubility and dissolution rate so that there is a high enough amount of the drug in solution with the first about 0.5 to 1.5 hours.

In another aspect, the present invention provides a solid pharmaceutical composition for oral administration comprising a substantially amorphous taxane, a hydrophilic, and preferably polymeric, carrier and a surfactant.

The advantage provided by the composition of this aspect is that the solubility of the taxane is increased by a surprising degree. Further, the rate of dissolution of the taxane is also increased to a surprising degree. Both of these factors result in a significant increase in the bioavailability of the taxane. It is thought that this is due, at least in part, to the taxane being in an amorphous state. Crystalline taxanes have very low solubilities. Further, in clinical trials, it was found that the oral compositions of the invention gave a high AUC, and an inter-individual variability which was significantly lower than the inter-individual variability demonstrated by a liquid formulation. This provides a much more predictable taxane exposure which is very desirable from a safety perspective in oral chemotherapy regimens. The intra-individual variability also appeared to be significantly lower. A further advantage is that the oral composition of the invention appears to be at least equally or better tolerated (i.e. in terms of side effects) than a liquid oral taxane solution.

An advantage provided by the carrier is that it helps to maintain the taxane in an amorphous state when it is placed in aqueous media. This helps to stop the taxane from crystallising or increases the length of time before the taxane starts to crystallise in solution. Therefore, the solubility and dissolution rate of the taxane remain high. Further, the carrier gives good physical and chemical stability to the composition. It helps to prevent the degradation of the taxane and also helps to prevent the substantially amorphous taxane from changing to a more crystalline structure over time in the solid state. The good physical stability ensures the solubility of the taxane remains high.

The surfactant also helps to maintain the taxane in an amorphous state when placed in aqueous media and, surprisingly, substantially increases the solubility of the taxane compared to compositions comprising an amorphous taxane and a carrier.

The term "substantially amorphous" means that there should be little or no long range order of the position of the taxane molecules. The majority of the molecules should be randomly orientated. A completely amorphous structure has no long range order and contains no crystalline structure whatsoever; it is the opposite of a crystalline solid. However, it can be hard to obtain a completely amorphous structure for some solids. Therefore, many "amorphous" structures are not completely amorphous but still contain a certain amount of long range order or crystallinity. For example, a solid may be mainly amorphous but have pockets of crystalline structure or may contain very small crystals so that it is bordering on being truly amorphous. Therefore, the term "substantially amorphous" encompasses solids which have some amorphous structure but which also have some crystalline structure as well. The crystallinity of the substantially amorphous taxane should be less than 50%. Preferably, the crystallinity of the substantially amorphous taxane is less than 40%, even more preferably, less than 30%, more preferably still, less than 25%, even more preferably, less than 20%, more preferably still, less than 15%, even more preferably, less than 12.5%, more preferably still, less than 10%, even more preferably, less than 7.5%, more preferably still, less than 5% and most preferably, less than 2.5%. Since crystalline taxanes have low solubility, the lower the crystallinity of the substantially amorphous taxane, the better the solubility of the substantially amorphous taxane.

The substantially amorphous taxane can be prepared in any suitable manner and techniques would be apparent to those skilled in the art. For example, it may be prepared using a solvent evaporation method or lyophilisation. Preferably, the amorphous taxane is prepared by lyophilisation. Surprisingly, it has been found that preparing the amorphous taxane using lyophilisation results in the composition having a better solubility and dissolution rate compared to an evaporation method. This is thought to be due to the lyophilisation method producing a more amorphous taxane compared to the solvent evaporation method.

The composition for oral administration is in a solid form. The solid composition can be in any suitable form as long as the taxane is in a substantially amorphous state. For example, the composition can comprise a physical mixture of amorphous taxane, carrier and surfactant. Preferably, the taxane and carrier are in the form of a solid dispersion. The term "solid dispersion" is well known to those skilled in the art and means that the taxane is partly molecularly dispersed in the carrier. More preferably, the taxane and carrier are in the form of a solid solution. The term "solid solution" is well known to those skilled in the art and means that the taxane is substantially completely molecularly dispersed in the carrier. It is thought that solid solutions are more amorphous in nature than solid dispersions. Methods of preparing solid dispersions and solid solutions are well known to those skilled in the art [93, 94]. Using these methods, both the taxane and carrier are in an amorphous state. When the taxane and carrier are in the form of a solid dispersion or solution, the solubility and dissolution rate of the taxane is greater than a physical mixture of amorphous taxane and carrier. It is thought that, when the taxane is in a solid dispersion or solution, the taxane is in a more amorphous state compared to amorphous taxane on its own. It is thought that this results in the improved solubility and dissolution. The crystallinity of the solid dispersion or solution should be less than 50%. Preferably, the crystallinity of the solid dispersion or solution is less than 40%, even more preferably, less than 30%, more preferably still, less than 25%, even more preferably, less than 20%, more preferably still, less than 15%, even more preferably, less than 12.5%, more preferably still, less than 10%, even more preferably, less than 7.5%, more preferably still, less than 5% and most preferably, less than 2.5%.

When the taxane and carrier are in a solid dispersion, the surfactant can be in a physical mixture with the solid dispersion or solution. Preferably, however, the composition comprises a taxane, carrier and surfactant in the form of a solid dispersion or, more preferably, a solid solution. The advantage of having all three components in a solid dispersion or solution is that it enables the use of a lower amount of surfactant to achieve the same improvement in solubility and dissolution rate.

In one embodiment, the composition can be contained in a capsule for oral administration. The capsule can be filled in a number of different ways. For example, the amorphous taxane may be prepared by lyophilisation, powdered, mixed with the carrier and surfactant, and then dispensed into the capsule. In an alternative preferable embodiment, the amorphous taxane is prepared by lyophilisation of a taxane solution in a capsule for oral administration. The taxane solution containing the required amount of taxane is dispensed into the capsule and then lyophilised whilst contained in the capsule. This makes it easier to dispense the required amount of taxane into the capsule as it is easier to dispense liquids rather than powders. It also eliminates a capsule filling step making the process more efficient. Powdered carrier and surfactant can then be added. Preferably, the capsule is an HPMC capsule.

If the taxane and carrier are in the form of a solid dispersion or solution, the solution containing the taxane and carrier is preferably dispensed into the capsule and then lyophilised whilst in the capsule. In this way, the solid dispersion or solution is prepared by lyophilisation of a taxane and carrier solution in a capsule for oral administration. This again eliminates a capsule filling step. Powdered surfactant can then be added.

If the taxane, carrier and surfactant are in the form of a solid dispersion or solution, the solution containing the taxane, carrier and surfactant is preferably dispensed into the capsule and then lyophilised whilst in the capsule. In this way, the solid dispersion or solution is prepared by lyophilisation of a taxane, carrier and surfactant solution in a capsule for oral administration. This again eliminates a capsule filling step and eliminates the need to handle powders which can be problematic.

The taxane of the composition can be any suitable taxane as defined above. Preferably, the taxane is selected from docetaxel, paclitaxel, BMS-275183, functional derivatives thereof and pharmaceutically acceptable salts or esters thereof. More preferably, the taxane is selected from docetaxel, paclitaxel, functional derivatives thereof and pharmaceutically acceptable salts or esters thereof.

The hydrophilic, and preferably polymeric, carrier of the composition is an organic, and preferably polymeric, compound capable of at least partial dissolution in aqueous media at pH 7.4 and/or capable of swelling or gelation in such aqueous media. The carrier can be any suitable hydrophilic, and preferably polymeric, carrier which ensures that the taxane remains in an amorphous state in the composition and increases the solubility and dissolution rate of the taxane. Preferably, the carrier is selected from: polyvinylpyrrolidone (PVP); polyethylene glycol (PEG); polyvinylalcohol (PVA); crospovidone (PVP-CL); polyvinylpyrrolidone-polyvinylacetate copolymer (PVP-PVA); cellulose derivatives such as methylcellulose, hydroxypropylcellulose, carboxymethylethylcellulose, hydroxypropylmethylcellulose (HPMC), cellulose acetate phthalate and hydroxypropylmethylcellulose phthalate; polyacrylates; polymethacrylates; sugars, polyols and their polymers such as mannitol, sucrose, sorbitol, dextrose and chitosan; and cyclodextrins. More preferably, the carrier is selected from PVP, PEG and HPMC, and most preferably, the carrier is PVP.

If the carrier is PVP, it can be any suitable PVP [98] to act as a carrier and to help keep the taxane in an amorphous state. For example, the PVP may be selected from PVP-K12, PVP-K15, PVP-K17, PVP-K25, PVP-K30, PVP-K60, PVP-K90 and PVP-K120. Preferably, the PVP is selected from PVP-K30, PVP-K60 and PVP-K90.

The composition can contain any suitable amount of the carrier relative to the amorphous taxane so that the carrier maintains the amorphous taxane in its amorphous state. Preferably, the taxane to carrier weight ratio is between about 0.01:99.99 w/w and about 75:25 w/w. More preferably, the taxane to carrier weight ratio is between about 0.01:99.99 w/w and about 50:50 w/w, even more preferably, between about 0.01:99.99 w/w and about 40:60 w/w, more preferably still, between about 0.01:99.99 w/w and about 30:70 w/w, even more preferably, between about 0.1:99.9 w/w and about 20:80 w/w, more preferably still, between about 1:99 w/w and about 20:80 w/w, even more preferably, between about 2.5:97.5 w/w and about 20:80 w/w, more preferably still, between about 2.5:97.5 w/w and about 15:85 w/w, even more preferably, between about 5:95 w/w and about 15:85 w/w and most preferably, about 10:90 w/w.

The surfactant can be any suitable pharmaceutically acceptable surfactant and such surfactants are well known to those skilled in the art. Preferably, the surfactant is selected from triethanolamine, sunflower oil, stearic acid, monobasic sodium phosphate, sodium citrate dihydrate, propylene glycol alginate, oleic acid, monoethanolamine, mineral oil and lanolin alcohols, methylcellulose, medium-chain triglycerides, lecithin, hydrous lanolin, lanolin, hydroxypropyl cellulose, glyceryl monostearate, ethylene glycol pamitostearate, diethanolamine, lanolin alcohols, cholesterol, cetyl alcohol, cetostearyl alcohol, castor oil, sodium dodecyl sulphate (SDS), sorbitan esters (sorbitan fatty acid esters), polyoxyethylene stearates, polyoxyethylene sorbitan fatty acid esters, polyoxyethylene castor oil derivatives, polyoxyethylene alkyl ethers, poloxamer, glyceryl monooleate, docusate sodium, cetrimide, benzyl bezoate, benzalkonium chloride, benzethonium chloride, hypromellose, non-ionic emulsifying wax, anionic emulsifying wax and triethyl citrate. More preferably, the surfactant is selected from sodium dodecyl sulphate (SDS), sorbitan esters (sorbitan fatty acid esters), polyoxyethylene stearates, polyoxyethylene sorbitan fatty acid esters, polyoxyethylene castor oil derivatives, polyoxyethylene alkyl ethers, poloxamer, glyceryl monooleate, docusate sodium, cetrimide, benzyl bezoate, benzalkonium chloride, benzethonium chloride, hypromellose, non-ionic emulsifying wax, anionic emulsifying wax and triethyl citrate. Most preferably, the surfactant is SDS.

Any suitable amount of surfactant can be used in the composition in order to improve the solubility and dissolution rate of the taxane. Preferably, the weight ratio of surfactant, to taxane and carrier combined, is between about 1:99 w/w and about 50:50 w/w, more preferably, between about 1:99 w/w and about 44:56 w/w, even more preferably, between about 1:99 w/w and about 33:67 w/w, more preferably still, between about 2:98 w/w and about 33:67 w/w, even more preferably, between about 2:98 w/w and about 17:83 w/w, more preferably still, between about 5:95 w/w and about 17:83 w/w and most preferably, about 9:91 w/w.

Alternatively, the weight ratio of surfactant to taxane is preferably between about 1:100 w/w and about 60:1 w/w, more preferably, between about 1:50 w/w and about 40:1 w/w, even more preferably, between about 1:20 w/w and about 20:1 w/w, more preferably still, between about 1:10 w/w and about 10:1 w/w, even more preferably, between about 1:5 w/w and about 5:1 w/w, more preferably still, between about 1:3 w/w and about 3:1 w/w, even more preferably, between about 1:2 w/w and about 2:1 w/w and most preferably, about 1:1 w/w.

The unit dose of the taxane contained in the composition will depend on the intended frequency of administration of the composition. Suitable dosages and frequency of administration are discussed above in relation to the taxane and ritonavir composition.

In one embodiment, the composition comprises an enteric coating. Suitable enteric coatings are described above. An enteric coating prevents the release of the taxane in the stomach and thereby prevents acid-mediated degradation of the taxane. Furthermore, it enables targeted delivery of the taxane to the intestines where the taxane is absorbed, thus ensuring that the limited time during which the taxane is present in solution (before crystallisation takes place) is only spent at sites where absorption is possible.

In one embodiment, the composition may further comprise one or more additional pharmaceutically active ingredients. Preferably, one or more of the additional pharmaceutically active ingredients is a CYP3A4 inhibitor. Suitable CYP3A4 inhibitors are discussed above. Preferably, the CYP3A4 inhibitor is ritonavir.

The pharmaceutical composition may comprise additional pharmaceutically acceptable adjuvants and vehicles which are well known to those skilled in the art. Pharmaceutically acceptable adjuvants and vehicles that may be used in the pharmaceutical compositions of this invention include, but are not limited to, ion exchangers, alumina, aluminium stearate, serum proteins, such as human serum albumin, buffer substances such as phosphates, glycerine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate and wool fat.

The pharmaceutical compositions can be orally administered in any orally acceptable dosage form including, but not limited to, capsules, tablets, a powder or coated granules. Tablets may be formulated to be immediate release, extended release, repeated release or sustained release. They may also, or alternatively, be effervescent, dual-layer and/or coated tablets. Capsules may be formulated to be immediate release, extended release, repeated release or sustained release. Lubricating agents, such as magnesium stearate, are also typically added. For oral administration in a capsule form, useful diluents include lactose and dried corn starch. For tablets and capsules, other pharmaceutical excipients that can be added are binders, fillers, filler/binders, adsorbents, moistening agents, disintegrants, lubricants, glidants, and the like. Tablets and capsules may be coated to alter the appearance or properties of the tablets and capsules, for example, to alter the taste or to colour coat the tablet or capsule.

Other pharmaceutically acceptable additives which may be added to the composition are well known to those skilled in the art, some of which are discussed above with regard to the composition according to the first aspect of the invention.

The present invention also provides the above composition for use in therapy.

Further, the present invention provides the above composition for use in the treatment of neoplastic disease. Suitable neoplastic diseases are discussed above.

The present invention also provides a method of treatment of a neoplastic disease, the method comprising the administration, to a subject in need of such treatment, of an effective amount of the above composition.

Preferably, the method is used to treat a human subject.

It will be appreciated by one skilled in the art that the composition of the invention comprising a substantially amorphous taxane and carrier can be used in the methods described above relating to the use of a taxane and a CYP3A4 inhibitor or ritonavir where appropriate.

In another aspect, the present invention provides a pharmaceutical composition for oral administration comprising a substantially amorphous taxane and a carrier, wherein the substantially amorphous taxane is prepared by lyophilisation.

The advantage provided by this composition is that it provides increased solubility of the taxane and also an increased dissolution rate. It is thought that this is because the lyophilisation method produces a more amorphous taxane compared to other methods of producing amorphous taxanes. It is thought that the more amorphous nature of the taxane provides the increased solubility and dissolution rate.

Additional optional features of the composition are the same as for the composition comprising an amorphous taxane, a carrier and a surfactant. For example, the composition comprising a substantially amorphous taxane and a carrier, wherein the substantially amorphous taxane is prepared by lyophilisation, preferably further comprises a surfactant. The preferred embodiments of the taxane, the carrier, the crystallinity of the taxane, the ratio of taxane to carrier, the state of the taxane and carrier, etc. are as defined above.

The present invention will now be described by way of example only with reference to the accompanying figures in which:

FIG. 1 is a graph showing docetaxel plasma concentration against time, comparing oral administration with ritonavir (RTV) (simultaneous, and with ritonavir given 60 mins prior to docetaxel) to i.v. administration (without ritonavir); Oral docetaxel dose: 100 mg. The commercially available i.v. docetaxel formulation (Taxotere®; 2 ml=80 mg docetaxel; excipient polysorbate 80) was diluted with ethanol 95%:water (13:87) to provide a 10 mg/ml docetaxel solution which the patients drank (10 ml of the 10 mg/ml solution) with 100 ml of tap water. Ritonavir dose: 1 capsule with 100 mg ritonavir (Norvir®).

FIG. 2 is a graph showing ritonavir plasma concentration against time, comparing oral administration of ritonavir (dose 100 mg; Norvir®, capsule) at the same time as oral docetaxel or 60 mins before oral docetaxel. T=0 is when docetaxel is administered. Therefore, the first part of the curve corresponding to ritonavir administered before docetaxel, is not visible. Oral docetaxel dose: 100 mg. The commercially available i.v. docetaxel formulation (Taxotere®; 2 ml=80 mg docetaxel; excipient polysorbate 80) was diluted with ethanol 95%:water (13:87) to provide a 10 mg/ml docetaxel solution which the patients drank (10 ml of the 10 mg/ml solution) with 100 ml of tap water. Ritonavir dose: 1 capsule with 100 mg ritonavir (Norvir®).

FIG. 3 is a pharmacokinetic model of oral docetaxel in combination with ritonavir (RTV). The different compartments in the pharmacokinetic model are as follows:

C1—gastrointestinal tract (input compartment of oral docetaxel)
C2—central compartment (docetaxel)
C3—first peripheral compartment (docetaxel)

C4—second peripheral compartment (docetaxel)
C5—gastrointestinal tract (input compartment of ritonavir)
C6—central compartment (ritonavir)
C7—active CYP3A4 enzyme
C8—inactive CYP3A4 enzyme;

Figure 11:
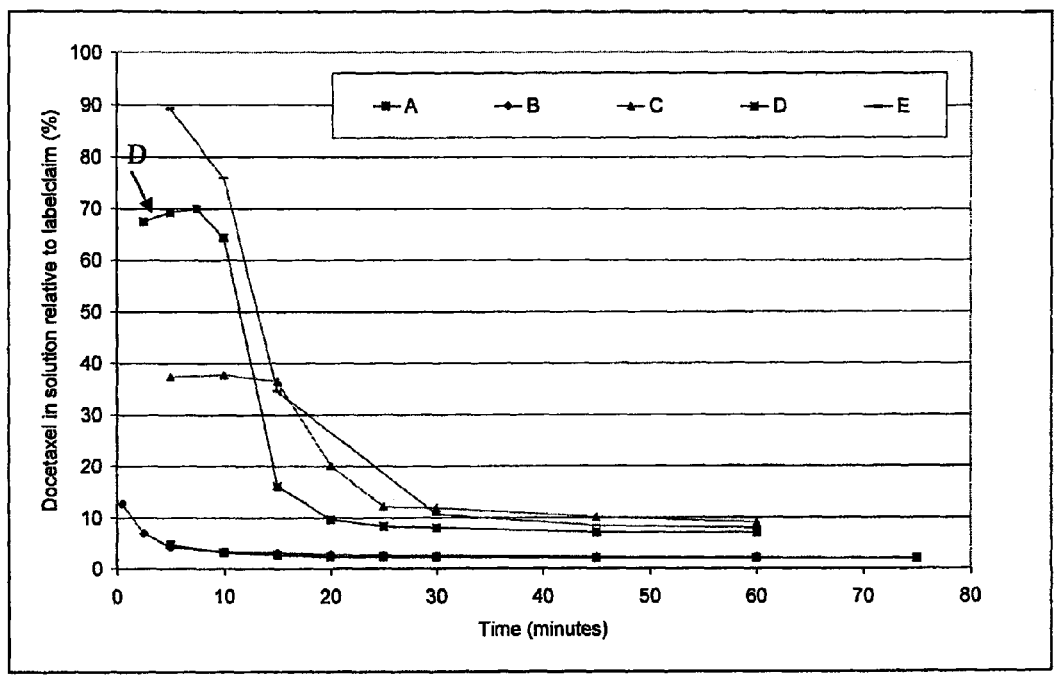
Figure 12:
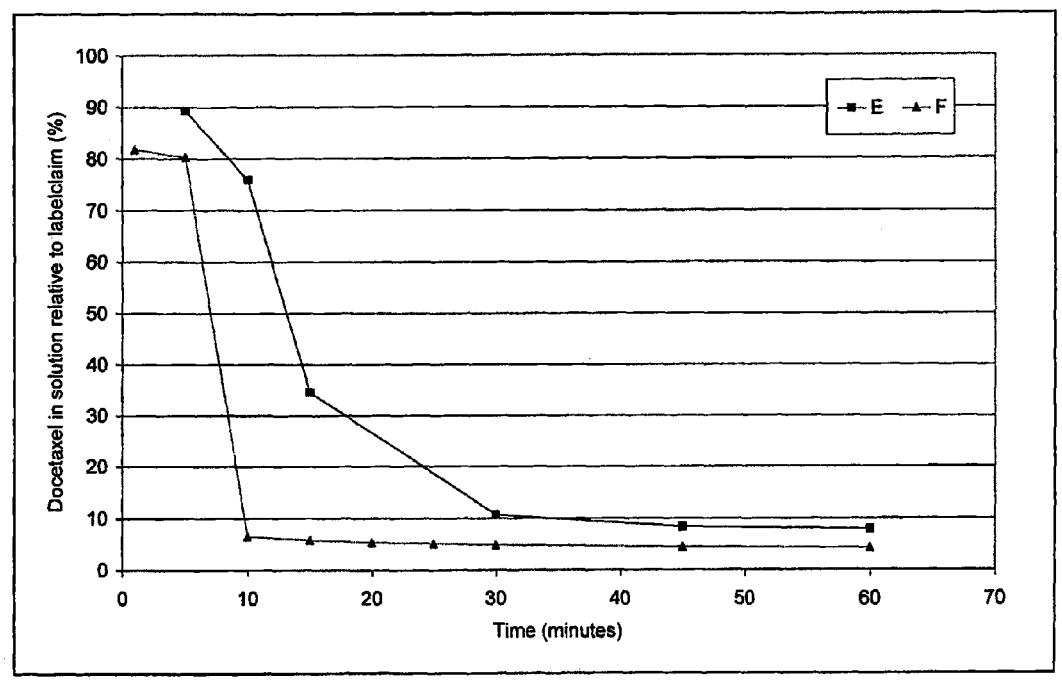
Figure 13:
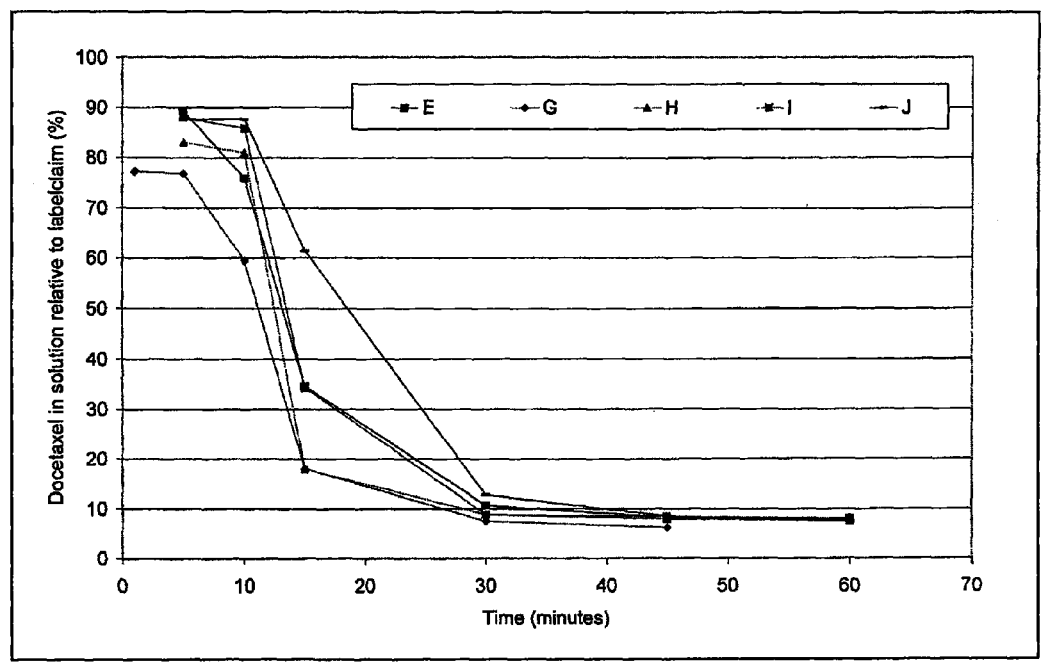
Figure 14:
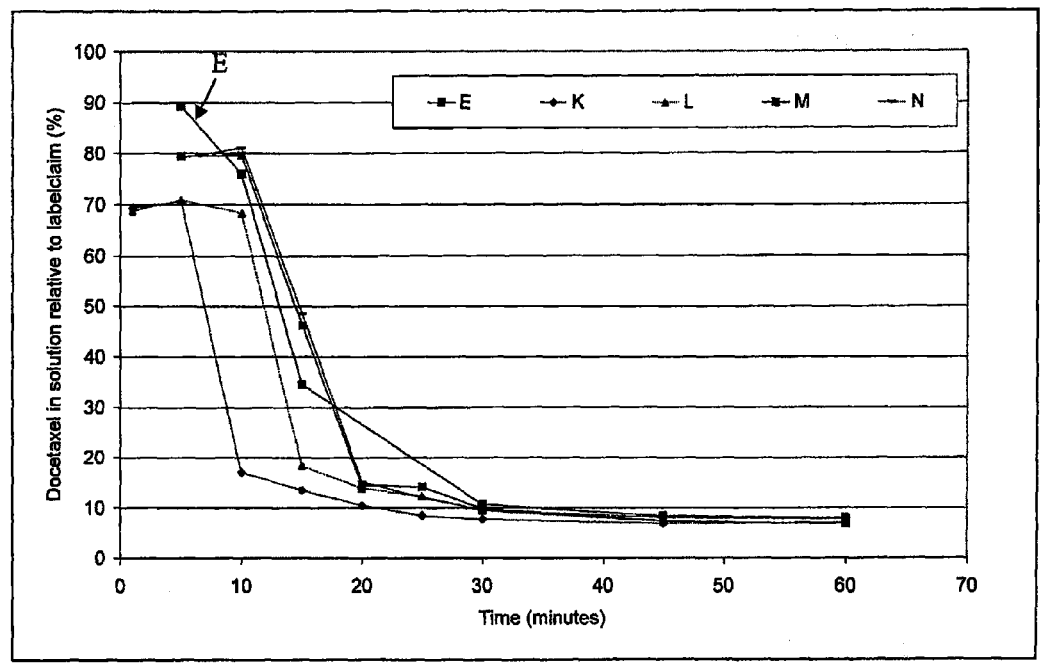
Figure 15:
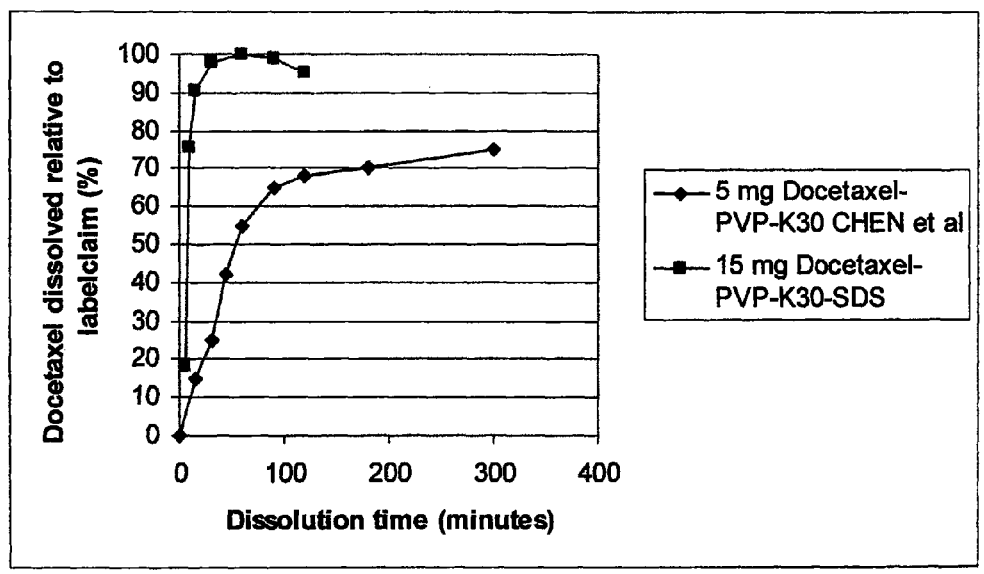
Figure 16:
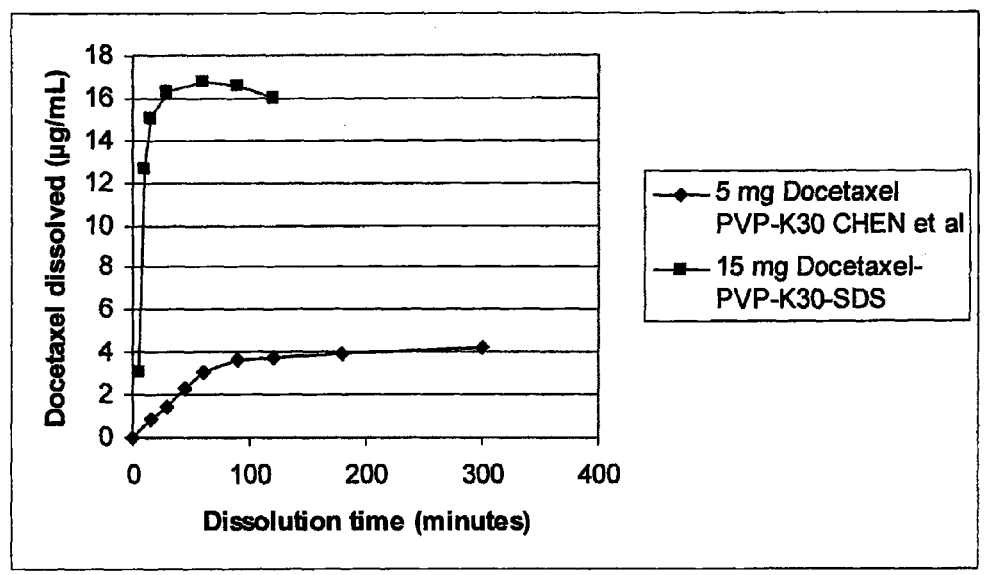
Figure 17:
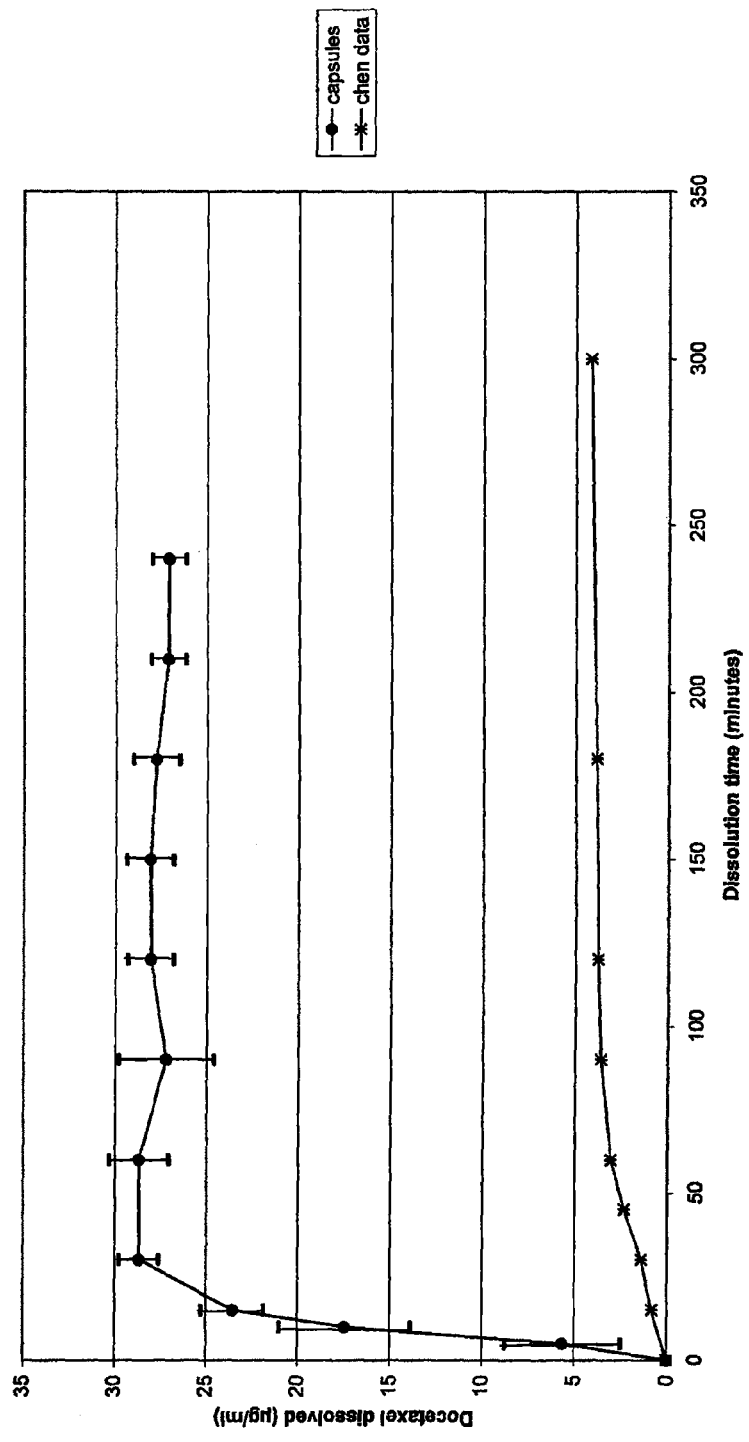

FIG. 11 shows the docetaxel solubility of five different formulations (see table 15). A: anhydrous docetaxel; B: amorphous docetaxel; C: physical mixture of anhydrous docetaxel, PVP-K30 and SDS; D: physical mixture of amorphous docetaxel, PVP-K30 and SDS; E: solid dispersion of amorphous docetaxel, PVP-K30 and SDS (dissolution conditions: ±6 mg docetaxel, 25 mL WfI, 37° C., 720 rpm);

FIG. 12 shows docetaxel solubility of solid dispersions with different carriers (see table 15). E: Solid dispersion of amorphous docetaxel, PVP-K30 and SDS; F: Solid dispersion of amorphous docetaxel, HPβ-CD and SDS. (Dissolution conditions: ±6 mg Docetaxel, 25 mL WfI, 37° C., 720 rpm);

FIG. 13 shows docetaxel solubility of solid dispersions with PVP of various chain lengths (see table 15). E: solid dispersion of amorphous docetaxel, PVP-K30 and SDS; G: solid dispersion of amorphous docetaxel, PVP-K12 and SDS; H: solid dispersion of amorphous docetaxel, PVP-K17 and SDS; I: solid dispersion of amorphous docetaxel, PVP-K25 and SDS; J: solid dispersion of amorphous docetaxel, PVP-K90 and SDS. (Dissolution conditions: ±6 mg Docetaxel, 25 mL WfI, 37° C., 720 rpm);

FIG. 14 shows docetaxel solubility of solid dispersions with various drug loads (see table 15). E: 1/11 docetaxel; K: 5/docetaxel; L: 1/3 docetaxel; M: 1/6 docetaxel; N: 1/21 docetaxel. (Dissolution conditions: ±6 mg Docetaxel, 25 mL WfI, 37° C., 720 rpm);

FIG. 15 shows the dissolution results in terms of the relative amount of docetaxel dissolved of a solid dispersion of docetaxel, PVP-K30 and SDS, compared to literature data of a solid dispersion of docetaxel and PVP-K30 [Chen et al., 95];

FIG. 16 shows the dissolution results in terms of the absolute amount of docetaxel dissolved of a solid dispersion of docetaxel, PVP-K30 and SDS, compared to literature data of a solid dispersion of docetaxel and PVP-K30 [Chen et al., 95];

FIG. 17 shows the results of a dissolution test of docetaxel capsules (15 mg docetaxel (DXT) per capsule with PVP-K30+SDS) compared with literature data (Chen et al. [95].

Figure 18:
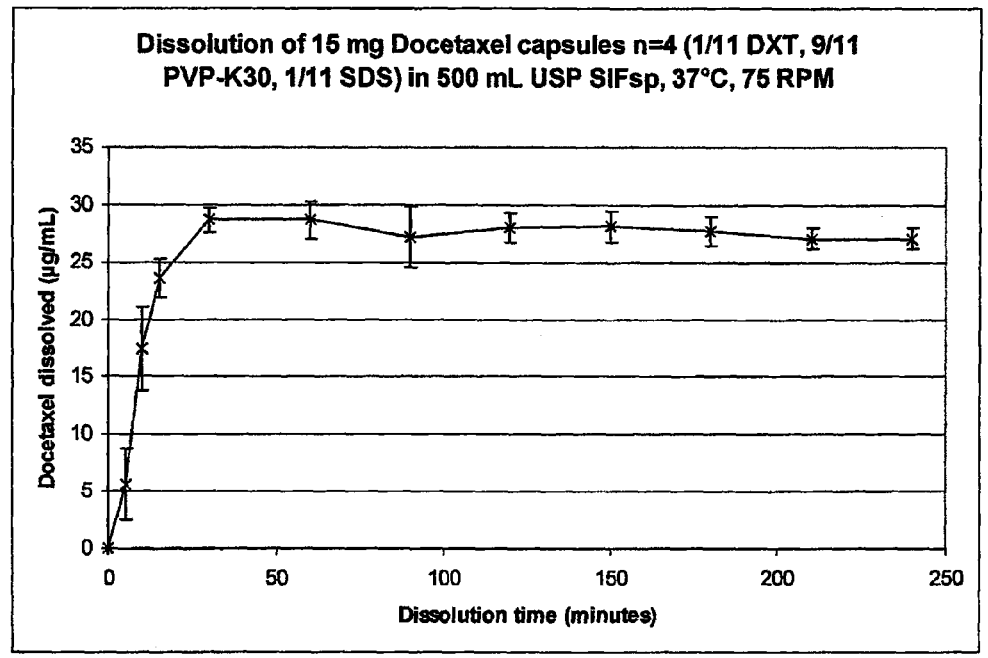
Figure 19:
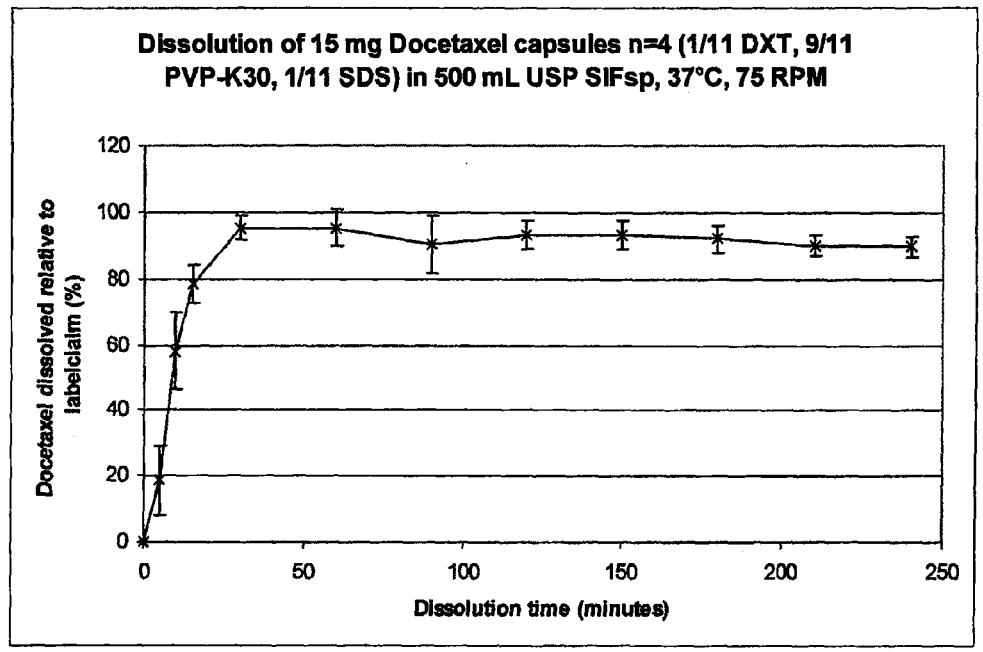
Figure 20:
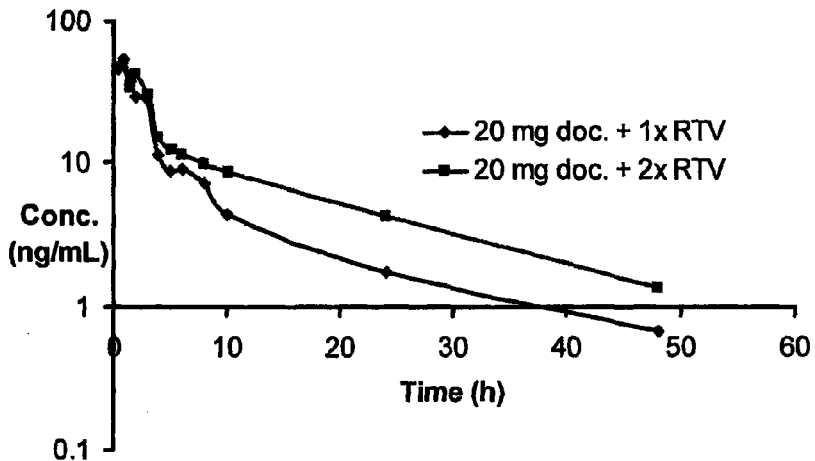
Figure 22:
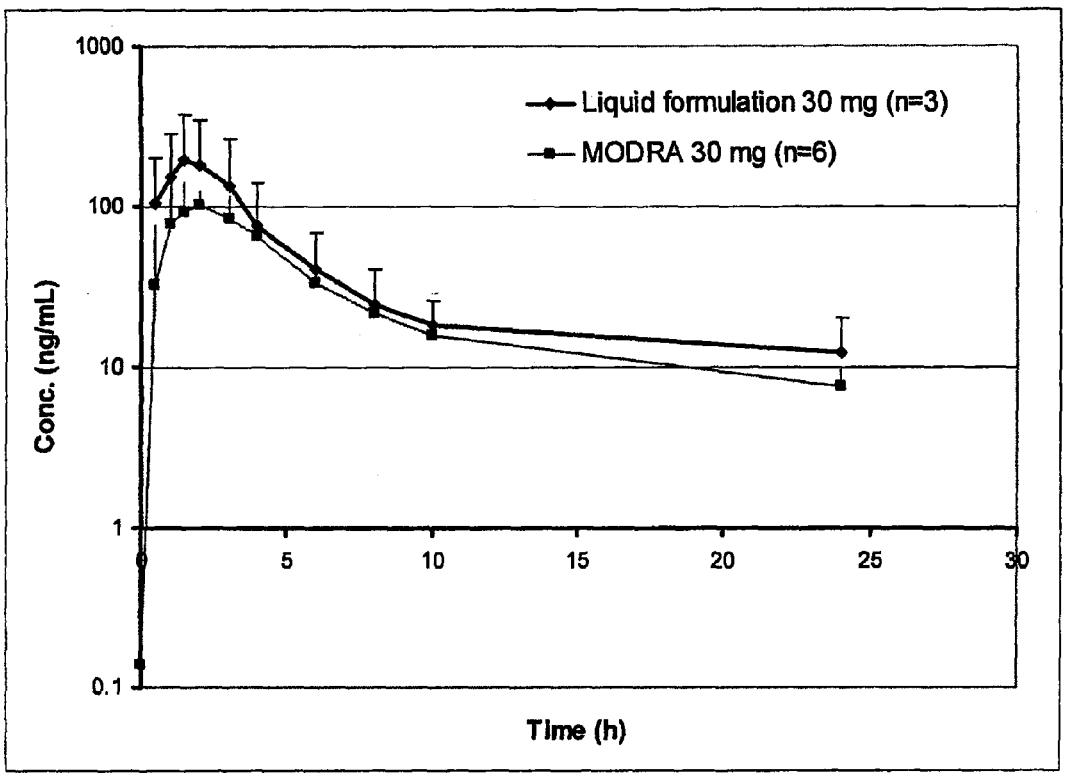
Figure 21:
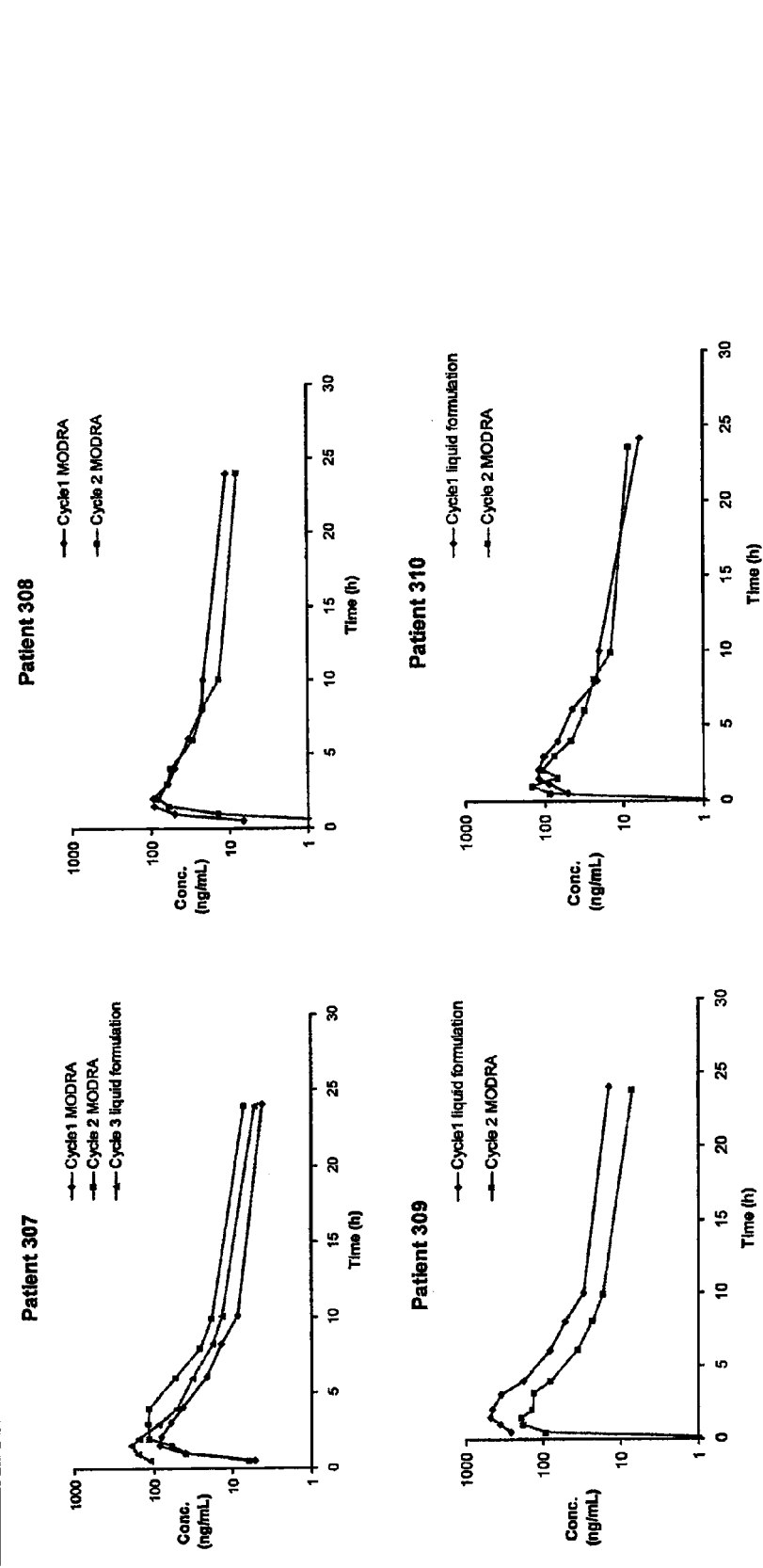
Figure 23:
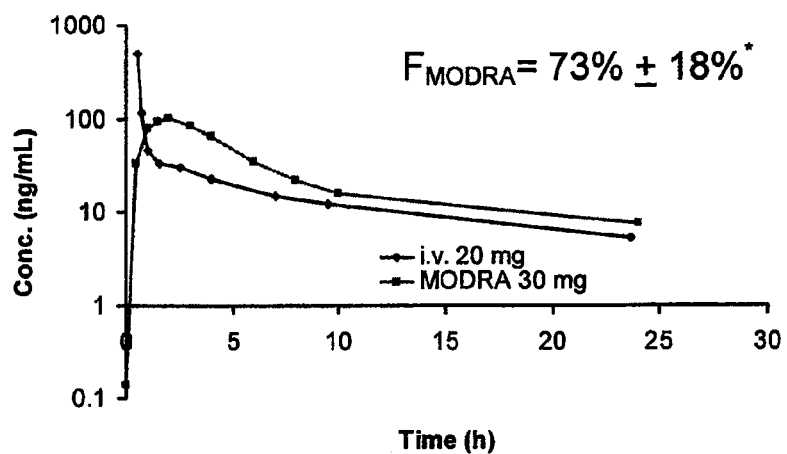

FIG. 18 shows the dissolution results in terms of the absolute amount of docetaxel dissolved of a solid dispersion of docetaxel, PVP-K30 and SDS. The dissolution test was carried out in Simulated Intestinal Fluid sine Pancreatin (SIFsp);

FIG. 19 shows the dissolution results in terms of the relative amount of docetaxel dissolved of a solid dispersion of docetaxel, PVP-K30 and SDS. The dissolution test was carried out in Simulated Intestinal Fluid sine Pancreatin (SIFsp);

FIG. 20 shows the pharmacokinetic curves of a patient who received docetaxel and ritonavir simultaneously in a first cycle. In the second cycle, the patient received docetaxel and ritonavir simultaneously at t=0 and then an additional booster dose of ritonavir at t=4 h;

FIG. 21 shows the pharmacokinetic curves of four patients who received a liquid formulation of docetaxel and/or a solid dispersion comprising docetaxel (referred to as MODRA);

FIG. 22 shows the pharmacokinetic curves of patients receiving the liquid oral formulation of docetaxel compared to the patients receiving the solid oral formulation of docetaxel (MODRA); and FIG. 23 shows pharmacokinetic curves after i.v. and oral administration of docetaxel. Both i.v. and oral docetaxel administration was combined with administration of ritonavir. N.B. The calculated bioavailability is corrected for the administered dose.

Example 1

A 100 mg ritonavir dose was combined with a 100 mg docetaxel dose and orally administered simultaneously to 22 patients. A comparison was made with i.v. administered docetaxel (100 mg) (Taxotere®) given as a 1 hour i.v. infusion (standard procedure) (without ritonavir).

Oral ritonavir: 1 capsule with 100 mg ritonavir (Norvir®). Oral docetaxel dose: 100 mg. The commercially available i.v. docetaxel formulation (Taxotere®; 2 ml=80 mg docetaxel; excipient polysorbate 80) was diluted with ethanol 95%:water (13:87) to provide a 10 mg/ml docetaxel solution which the patients drank (10 ml of the 10 mg/ml solution) with 100 ml of tap water.

The pharmacokinetic data that were obtained are as follows:

| | |
|---|---|
| AUC docetaxel oral without ritonavir | 0.29 ± 0.26 (mg · h/L) |
| AUC docetaxel oral with ritonavir | 2.4 ± 1.5 (mg · h/L) |
| AUC docetaxel intravenous without ritonavir | 1.9 ± 0.4 (mg · h/L) |

The results show a dual effect of ritonavir on both docetaxel absorption and elimination. Docetaxel AUC increases 8.2 fold when given orally in combination with ritonavir. Surprisingly, the exposure is even higher than that reached after intravenous administration reflecting the additional ritonavir effect on inhibition of docetaxel elimination.

Conclusions

The concept has been clearly proven in patients that ritonavir can increase the systemic exposure of oral docetaxel to levels that are comparable to or even higher than the levels after intravenous administration of docetaxel at the same dose level. The combination appears to be safe with very favourable pharmacokinetic characteristics.

Example 2

Treatment of solid malignancies with the oral combination of docetaxel and ritonavir. Patients were randomized into two treatment groups, X and Y. Group X received, in the first week, 100 mg of ritonavir followed 60 minutes later by 100 mg oral docetaxel and, in the second week, these patients received 100 mg ritonavir and 100 mg oral docetaxel simultaneously. Patients in group Y received, in the first week, 100 mg ritonavir and 100 mg oral docetaxel simultaneously and, in the second week, 100 mg ritonavir followed 60 minutes later by 100 mg oral docetaxel. Both groups X and Y received 100 mg i.v. docetaxel (Taxotere®; standard procedure; as 1 hour infusion) without ritonavir 15 days after the commencement of oral administration.

Oral docetaxel dose: 100 mg. The commercially available i.v. docetaxel formulation (Taxotere®; 2 ml=80 mg docetaxel; excipient polysorbate 80) was diluted with ethanol 95%: water (13:87) to provide a 10 mg/ml docetaxel solution which the patients drank (10 ml of the 10 mg/ml solution) with 100 ml of tap water. Ritonavir dose: 1 capsule with 100 mg ritonavir (Norvir®).

The pharmacokinetic results are given below:

TABLE 1A

DOCETAXEL

| Patient | AUC (mg × h/L) | | | F (%)[1] | |
|---|---|---|---|---|---|
| | Simultaneous | 60 min interval | IV day 15 | Simultaneous | 60 min interval |
| 101 (X) | 5.6 | 4.1 | 1.7 | 329 | 241 |
| 102 (Y) | 1.6 | 2.6 | 1.8 | 89 | 144 |
| 103 (Y) | 2.2 | 4.6 | 1.8 | 122 | 256 |
| 105 (X) | 2.8 | 3.3 | 2.1 | 133 | 157 |
| 106 (Y) | 2.4 | 3.9 | 1.4 | 171 | 279 |
| 107 (Y) | 2.4 | 2.1 | 2.6 | 92 | 81 |
| 108 (X) | 1.1 | 1.4 | 1.4 | 79 | 100 |
| 110 (X) | 0.7 | 0.6 | 2.2 | 32 | 27 |
| Mean ± SD | 2.4 ± 1.5 | 2.8 ± 1.4 | 1.9 ± 0.4 | 131 ± 90 | 161 ± 91 |

[1] F (apparent) determined by (AUCpo/AUC iv) × (dose iv/dose po) × 100%

TABLE 1B

DOCETAXEL

| Patient | Cmax (mg/L) | | | Tmax (h) | | |
|---|---|---|---|---|---|---|
| | Simultaneous | 60 min interval | IV day 15 | Simultaneous | 60 min interval | IV day 15 |
| 101 (X) | 0.71 | 0.58 | 1.47 | 3.3 | 3.0 | 1.0 |
| 102 (Y) | 0.21 | 0.42 | 1.52 | 4.0 | 2.0 | 1.0 |
| 103 (Y) | 0.20 | 0.72 | 1.3 | 4.0 | 3.0 | 0.8 |
| 105 (X) | 0.36 | 0.34 | 1.6 | 4.0 | 4.0 | 1.0 |
| 106 (Y) | 0.42 | 0.91 | 1.1 | 2.0 | 2.0 | 0.8 |
| 107 (Y) | 0.26 | 0.50 | 1.5 | 3.0 | 1.5 | 1.0 |
| 108 (X) | 0.26 | 0.19 | 1.0 | 2.1 | 3.0 | 0.8 |
| 110 (X) | 0.10 | 0.11 | 1.6 | 1.0 | 1.5 | 0.8 |
| Mean ± SD | 0.32 ± 0.2 | 0.47 ± 0.3 | 1.4 ± 0.2 | 2.9 ± 1.1 | 2.5 ± 0.9 | 0.9 ± 0.1 |

Conclusions

Figure 1:
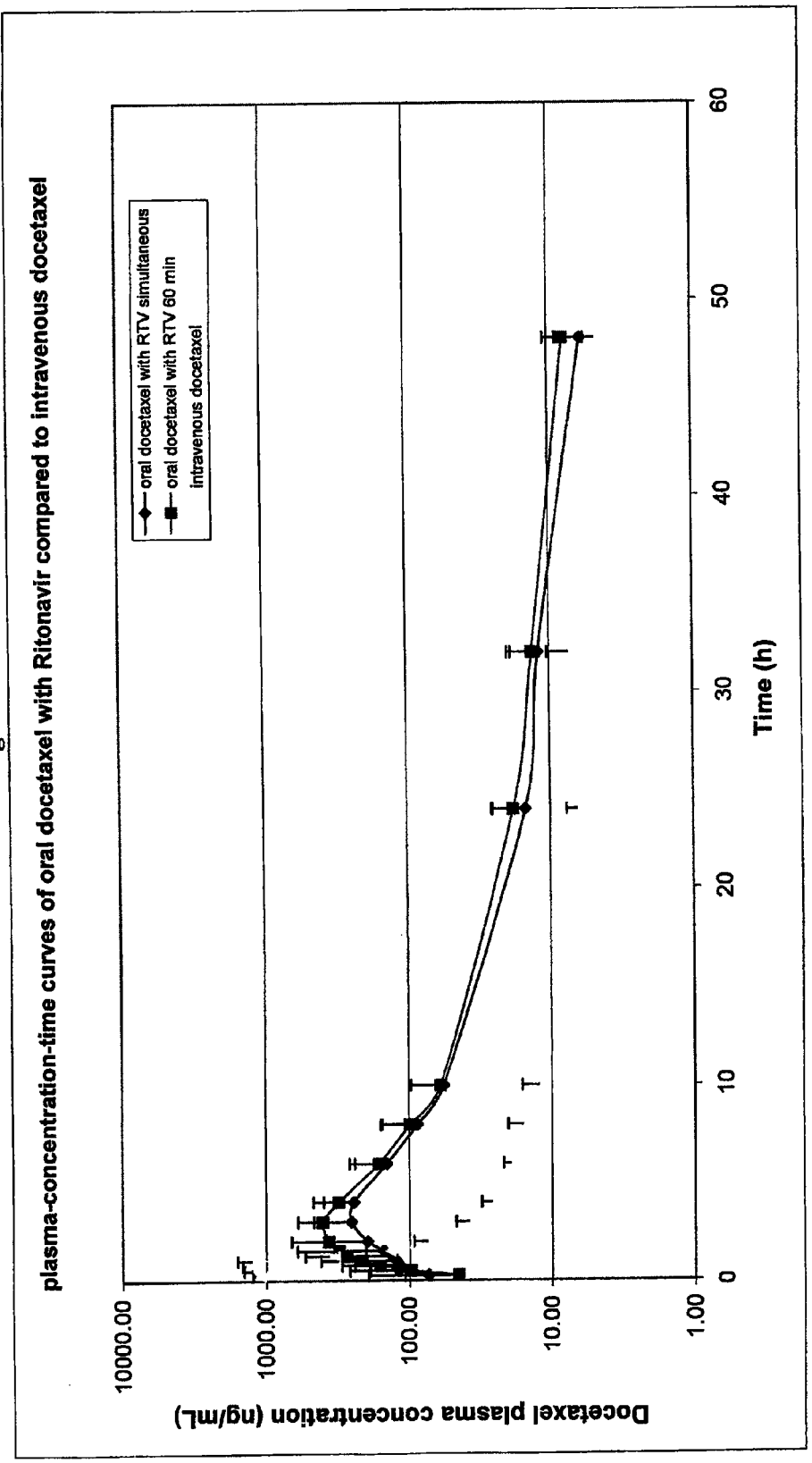

There is no significant difference between simultaneous administration of docetaxel and ritonavir compared with ritonavir administered 60 minutes before the docetaxel. The AUC for oral administration is greater than the AUC for intravenous administration (see FIG. 1). This is explained by the effects of ritonavir on inhibition of docetaxel elimination.

Remarks

This clinical study was executed with relatively low doses of docetaxel, but yielding high AUC values (2.4±1.5 mg·h/L; 100 mg docetaxel) and which are even higher than the AUC values after intravenous administration of the same dose. With that, it has to be realised that the distribution volume after the oral route is larger (shortly after administration) than after the intravenous route because the pharmaceutical vehicle, present after intravenous administration but not reaching the systemic circulation after oral administration, limits tissue distribution of docetaxel. The inventors have built a pharmacokinetic model to understand these effects (see below). The model also demonstrates that the ritonavir effect on docetaxel elimination has gone when ritonavir is not present anymore in the bloodstream. Ritonavir inhibits docetaxel clearance down to 35% of the level thereof in the absence of ritonavir.

Compared to the doses used in the prior art preclinical study in mice, this clinical study used 100 mg ritonavir and 100 mg docetaxel whereas the pre-clinical study in mice used 12.5 mg/kg ritonavir and 10-30 mg/kg docetaxel. Docetaxel doses of 10-30 mg/kg are extremely toxic (life threatening) in humans. Ritonavir doses of 12.5 mg/kg are substantially higher than would normally be used in humans to inhibit CYP3A4.

In the prior art preclinical study, ritonavir was given 30 minutes in advance of docetaxel. In the clinical study the drugs were also administered simultaneously with no significant difference for the improvement in docetaxel pharmacokinetics, between simultaneous and 60 minutes prior administration of ritonavir. This indicates that both drugs can be given in a single pharmaceutical form (e.g. tablet, capsule or drinking solution containing both docetaxel and ritonavir).

The docetaxel AUC values (2.4±1.5 mg·h/L) obtained (with 100 mg docetaxel dose) when co-administered with 100 mg ritonavir, can be considered therapeutically active in a weekly schedule, for example, in metastatic breast cancer. This compares well with an earlier phase II trial where 100 mg docetaxel was given orally with CsA at a dose of 15 mg/kg, in a weekly schedule and leading to an overall response rate of 50% of patients with metastatic breast cancer, with docetaxel AUCs of about 2.3 mg·h/L.

Figure 2:
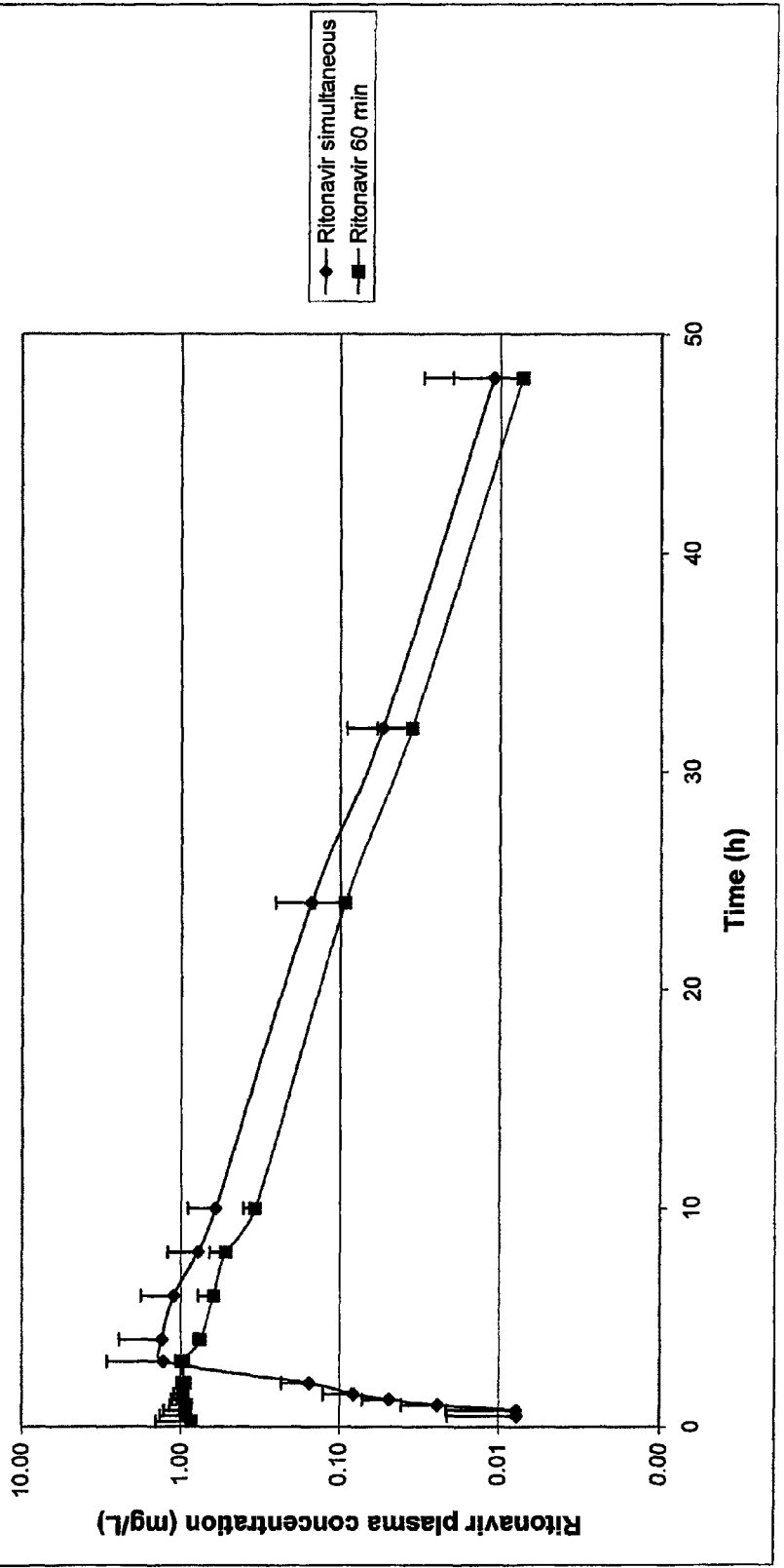

Ritonavir pharmacokinetic data are given below for completeness (see FIG. 2):

TABLE 2

RITONAVIR

| Patient | AUC (mg · h/L) | | Cmax (mg/L) | | Tmax (h) | |
|---|---|---|---|---|---|---|
| | Simultaneous | 60 min interval | Simultaneous | 60 min interval | Simultaneous | 60 min interval |
| 101 (X) | 23.2 | 11.8 | 3.1 | 1.3 | 3.3 | 0.3 |
| 102 (Y) | 7.3 | 8.9 | 0.8 | 1.1 | 4.0 | 0.5 |
| 103 (Y) | 13.5 | 14.1 | 0.7 | 1.1 | 6.0 | 3.0 |
| 105 (X) | 8.8 | 9.4 | 0.6 | 0.7 | 6.0 | 6.0 |
| 106 (Y) | 13.3 | 13.4 | 1.5 | 1.3 | 3.0 | 1.0 |
| 107 (Y) | 5.2 | 5.7 | 0.3 | 0.8 | 3.0 | 0.5 |
| 108 (X) | 2.6 | 4.2 | 0.2 | 0.5 | 2.1 | 2.0 |
| 110 (X) | 1.9 | 0.5 | 0.2 | 0.03 | 3.1 | 1.5 |
| Mean ± SD | 9.5 ± 7.0 | 8.5 ± 4.7 | 0.9 ± 0.97 | 0.9 ± 0.44 | 3.8 ± 1.4 | 1.9 ± 1.9 |

Pharmacokinetic Profile

Pharmacokinetic (PK) analysis of the data generated from the above trial was performed using the NONMEM (non-linear mixed effect modelling) program (GloboMax LLC, Hanover, Md., USA) to produce a pharmacokinetic profile. This models the absorption, elimination and distribution of a drug using different compartments. The pharmacological differences between oral and intravenous administration are presented below.

Oral docetaxel exposure was examined following single doses of docetaxel alone and in combination with ritonavir. Ritonavir was administered simultaneously or one hour before oral docetaxel.

After drug administration blood samples were collected for pharmacokinetic analyses. A blank sample was taken before dosing. Blood samples were centrifuged, plasma was separated and immediately stored at −20° C. until analyses. Analysis were performed with validated HPLC methods in a GLP (Good Laboratory Practice) licensed laboratory. This concerns all pharmacokinetic studies presented here by the inventors.

PK Model

Figure 3:
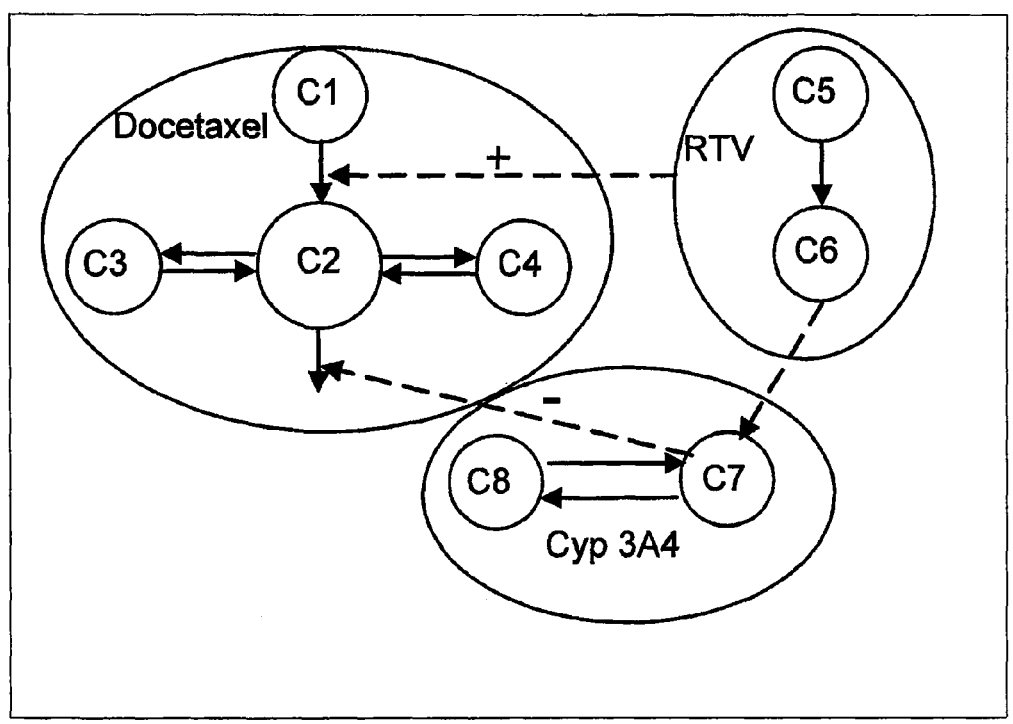

The PK model was based on the PK model of i.v. docetaxel. This model uses three compartments and is well described by Bruno et al. [85]. The data generated from orally administered docetaxel were implemented within this model, adding an additional depot compartment modelling for the gastrointestinal tract. The pharmacokinetic model for ritonavir was best described using a 2 compartment model, described by Kappelhoff et. al. [87]. FIG. 3 shows the final pharmacokinetic model schematically. The influence of ritonavir on the pharmacokinetics of docetaxel was modelled via two different mechanisms: a) improvement in the absorption of docetaxel in the presence of ritonavir (line connecting ritonavir (RTV) compartments with absorption of docetaxel from C1 to C2); b) ritonavir inhibits active CYP3A4 (line connecting C6 with C7) and active CYP3A4 is responsible for the elimination of docetaxel (line connecting C7 with the elimination route of docetaxel).

Absorption

Absorption of docetaxel markedly improved when co-administered with ritonavir. The calculated bioavailability for oral docetaxel alone is 14% (based on data of 3 patients who received 100 mg oral docetaxel). The bioavailability of oral docetaxel in combination with ritonavir was 4 times higher at 56%. This effect can be credited to the inhibition of CYP3A4 enzymes present in the GI tract by ritonavir.

Elimination

Figure 4:
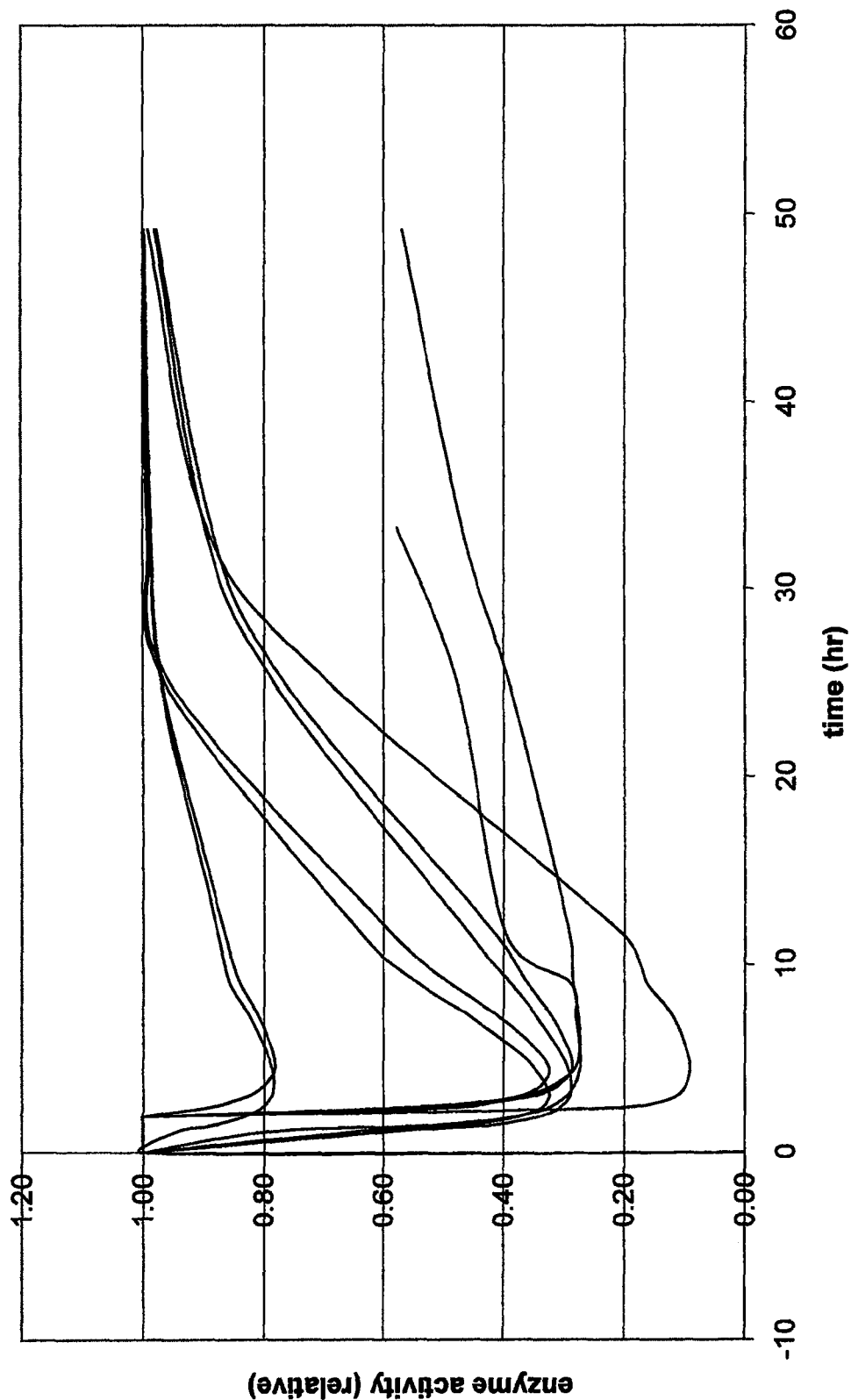
FIG. 4 is a graph showing, for a number of subjects, each line representing one subject, the relative amount of active CYP3A4 enzyme against time for oral docetaxel in combination with ritonavir.

Docetaxel is primarily metabolised by CYP3A4. Ritonavir inhibits CYP3A4. This results in decreased elimination when ritonavir is co-administered with docetaxel. The clearance of docetaxel correlates with the amount CYP3A4 and thus varies over time. FIG. 4 shows the estimated relative enzyme concentration over time. The clearance of docetaxel correlates 1:1 with the enzyme concentration. Therefore, a graph of the clearance of docetaxel versus time would be similar to FIG. 4.

Distribution Volume

The volume of the central compartment (C2 in FIG. 3) differs markedly between i.v. (+/−6 L) and oral (+/−60 L) administration. This is probably due to polysorbate 80, one of the main excipients of the docetaxel formulation. Polysorbate 80 forms micelles which are able to entrap docetaxel [86]. Polysorbate 80 enters the circulation in the case of i.v. administration but is not absorbed in the case of oral administration. Therefore, polysorbate does not affect the pharmacokinetic behaviour of docetaxel after oral administration due to the fact that it is not absorbed.

Conclusions

Bioavailability of oral docetaxel increased approximately 4 times when co-administered with ritonavir. Systemic exposure, in terms of AUC, increased 8.2 times, due to the combined effect of ritonavir on CYP3A4 in the GI tract and the liver (i.e. absorption and elimination, respectively).

Elimination of docetaxel is decreased when combined with ritonavir.

The distribution volume (the volume of the central compartment) is small in the presence of polysorbate 80 and large without polysorbate 80.

In the oral docetaxel studies mentioned above the commercially available i.v. docetaxel formulation (Taxotere®; 2 ml=80 mg docetaxel; excipient polysorbate 80) was diluted with ethanol 95%:water (13:87) to provide a 10 mg/ml docetaxel solution. This solution, prepared by the pharmacist, was ingested orally by the patients (10 ml of the 10 mg/ml solution for a 100 mg dose) as a drinking solution combined with 100 ml of tap water. For investigational purposes this is feasible, however, it is not for routine use and at home. Preparation of the drinking solution by the pharmacist is time-consuming. The solution has limited stability. Patients often complained of an unpalatable and unpleasant taste of the drinking solution (probably due to polysorbate and ethanol excipients). Evidently, an oral solid dosage form (e.g. taken as capsule or tablet) is preferred and much more patient friendly.

In summary, the present invention improves the bioavailability and systemic exposure of taxanes, improves the clinical efficacy of taxanes, especially oral taxanes, and probably also reduces the possible side effects associated with the treatment. This is economically and clinically beneficial.

Example 3

Oral Formulations of Paclitaxel 3.1: Solid Dispersion Versus Physical Mixture

In this experiment the solubility and dissolution rate of a composition comprising a solid dispersion of paclitaxel and PVP-K17 mixed with SDS was compared to a physical mixture of anhydrous paclitaxel, PVP-K17 and SDS.

5 mg Capsules of Paclitaxel Solid Dispersions in PVP-K17

A solid dispersion of 20% paclitaxel in PVP-K17 was prepared by dissolving 100 mg of paclitaxel in 10 mL t-butanol and 400 mg PVP-K17 in 6.67 mL water. The paclitaxel/t-butanol solution was added to the PVP-K17/water solution under constant stirring. The final mixture was transferred to 8 mL vials with a maximum fill level of 2 mL. t-butanol and water were subsequently removed by lyophilisation (see table 3 for conditions). 25 mg of a paclitaxel 20%/PVP-K17 solid dispersion (=5 mg paclitaxel) was mixed with 125 mg Lactose, 30 mg sodium dodecyl sulphate, and 30 mg croscarmellose sodium. The resulting powder mixture was encapsulated (see table 4).

TABLE 3 lyophilisation conditions: Lyovac GT4 (AMSCO/Finn-Aqua)

| Step | Time (hh:mm) | Shelve temperature (° C.) | Room pressure (%) | Maximum pressure (%) |
|---|---|---|---|---|
| 1 | 00:00 | Ambient | 100 | 100 |
| 2 | 01:00 | −35 | 100 | 100 |
| 3 | 03:00 | −35 | 100 | 100 |
| 4 | 03:01 | −35 | 40 | 50 |
| 5 | 48:00 | −35 | 40 | 50 |
| 6 | 63:00 | 25 | 40 | 50 |
| 7 | 66:00 | 25 | 40 | 50 |

TABLE 4 formulation of 5 mg paclitaxel/PVP-K17 solid dispersion capsules

| Component | Amount (mg) |
|---|---|
| paclitaxel (inside the solid dispersion) | 5 mg |
| PVP-K17 (inside the solid dispersion) | 20 mg |
| Lactose monohydrate | 125 mg |
| sodium dodecyl sulphate | 30 mg |
| croscarmellose sodium | 30 mg |

5 mg Capsules of Paclitaxel in a Physical Mixture with PVP-K17

A physical mixture was prepared by mixing 5 mg anhydrous paclitaxel with 20 mg PVP, 125 mg lactose, 30 mg sodium dodecyl sulphate, and 30 mg croscarmellose sodium. The resulting powder mixture was encapsulated.

TABLE 5 formulation of 5 mg paclitaxel/PVP-K17 physical mixture capsules

| Component | Amount (mg) |
|---|---|
| paclitaxel | 5 mg |
| PVP-K17 | 20 mg |
| Lactose monohydrate | 125 mg |
| sodium dodecyl sulphate | 30 mg |
| croscarmellose sodium | 30 mg |

Dissolution Test

Both capsule formulations were tested in 900 mL of Water for Injection maintained at 37° C. in a USP 2 (paddle) dissolution apparatus with a rotation speed of 75 rpm. In the first experiment, one capsule of each formulation was used. In the second experiment, two capsules of each formulation were used. Samples were collected at various timepoints and analyzed by HPLC-UV (see table 4).

TABLE 6

| chromatographic conditions | |
|---|---|
| Column | Apex octyl 150 × 4.6 mm 5 μm |
| Eluens | Methanol/Acetonitrile/0.02 M Ammoniumacetate 1/4/5 v/v/v |
| Flow | 1.0 mL/min |
| Injection volume | 50 μL |
| Run time | 15 minutes |
| Detection wavelength | 227 nm |

Results and Conclusions

Figure 5:
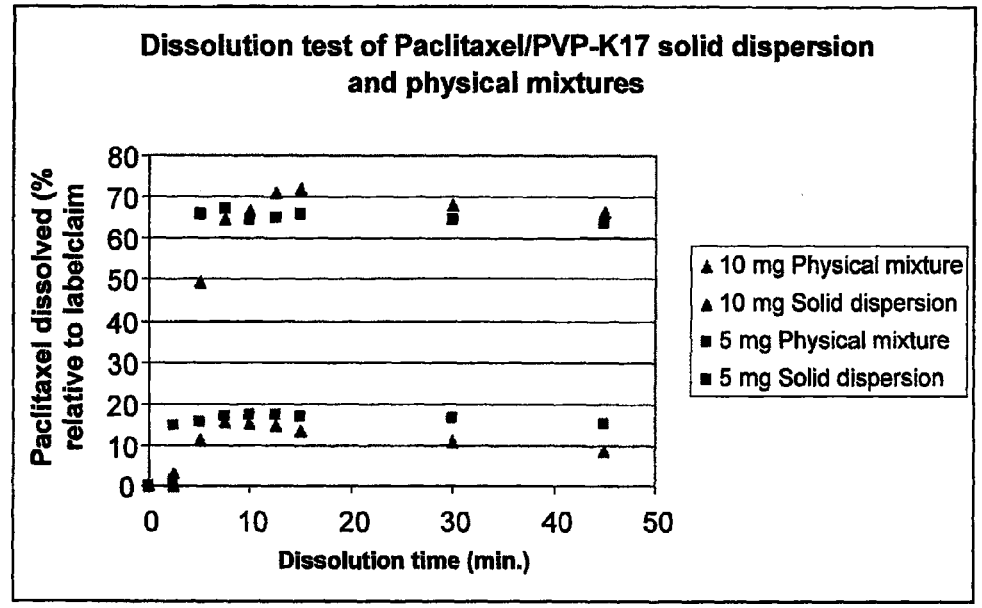
FIG. 5 shows the results of a dissolution test of paclitaxel solid dispersions versus paclitaxel physical mixtures (conditions: 900 mL WfI, 37° C., 75 rpm)

The results are shown in FIG. 5. The amount of paclitaxel dissolved is expressed relative to the label claim (5 and 10 mg). It can clearly be seen that the dissolution of paclitaxel is greatly improved by the incorporation in a solid dispersion with PVP. The maximum amount of paclitaxel dissolved stays below 20% relative to label claim when a physical mixture is used. When a solid dispersion is used, the solubility is about 65% (5 mg paclitaxel) or over 70% (10 mg paclitaxel). For the 10 mg paclitaxel experiment, this corresponds to an absolute solubility of about 8 μg/ml and this is achieved after about 15 minutes. Therefore, the solid dispersion significantly increases the solubility and also provides a rapid dissolution rate, both of which are important for bioavailability.

In a solid solution or solid dispersion, the amorphous state of the carrier enables thorough mixing of the carrier and taxane. The carrier prevents crystallization during storage as well as during dissolution in aqueous media.

3.2: Addition of Sodium Dodecyl Sulphate to the Capsule Formulation

In this experiment, the effect on solubility of the presence or absence of the surfactant SDS in the capsule was determined.

20% Paclitaxel Solid Dispersion in PVP-K17

A solid dispersion was prepared by dissolving 100 mg of Paclitaxel in 10 mL t-butanol and 400 mg PVP-K17 in 6.67 mL water. The paclitaxel/t-butanol solution was added to the PVP-K17/water solution under constant stirring. The final mixture was transferred to 8 mL vials with a maximum fill level of 2 mL. t-butanol and water were subsequently removed by lyophilisation (see table 3).

5 mg Paclitaxel Capsules without Sodium Dodecyl Sulphate 25 mg of a paclitaxel 20%/PVP-K17 solid dispersion (=5 mg paclitaxel) was mixed with 125 mg Lactose and encapsulated (see table 7).

TABLE 7 formulation of 5 mg paclitaxel/PVP-K17 solid dispersion without sodium dodecyl sulphate capsules

| Component | Amount (mg) |
|---|---|
| paclitaxel (inside the solid dispersion) | 5 mg |
| PVP-K17 (inside the solid dispersion) | 20 mg |
| Lactose monohydrate | 125 mg |

5 mg Paclitaxel Capsules with Sodium Dodecyl Sulphate 25 mg of a paclitaxel 20%/PVP-K17 solid dispersion (=5 mg paclitaxel) was mixed with 125 mg Lactose, 30 mg sodium dodecyl sulphate, and 30 mg croscarmellose sodium. The resulting powder mixture was capsulated (see table 8).

TABLE 8 formulation of 5 mg paclitaxel/PVP-K17 solid dispersion with sodium dodecyl sulphate capsules

| Component | Amount (mg) |
|---|---|
| paclitaxel (inside the solid dispersion) | 5 mg |
| PVP-K17 (inside the solid dispersion) | 20 mg |
| Lactose monohydrate | 125 mg |
| sodium dodecyl sulphate | 30 mg |
| croscarmellose sodium | 30 mg |

Dissolution Test

Both capsule formulations were tested in 900 mL of Water for Injection maintained at 37° C. in a USP 2 (paddle) dissolution apparatus with a rotation speed of 75 rpm. Samples were collected at various timepoints and analyzed by HPLC-UV (see table 6).

Results and Conclusions

Figure 6:
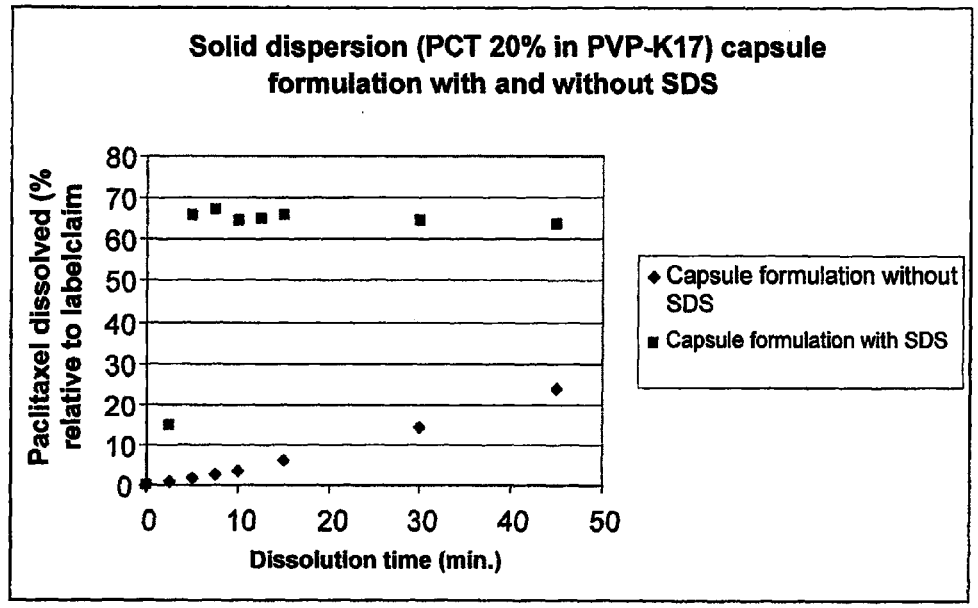
FIG. 6 shows the results of a dissolution test of paclitaxel (PCT) solid dispersion capsules with and without sodium dodecyl sulphate (conditions: 900 mL WfI, 37° C., 75 rpm)

The results are shown in FIG. 6. The amount of paclitaxel dissolved is expressed relative to the label claim (in this case 5 mg). The porosity of the lyophilized taxane and carrier solid dispersion was high enough to ensure rapid dissolution when in powder form (results not shown). However, when the powder is compressed in capsules, the wettability is dramatically decreased. Therefore, a surfactant is needed to wet the solid dispersion when it is compressed in capsules or tablets.

It can clearly be seen from FIG. 6 that the dissolution of paclitaxel is greatly improved by the addition of the surfactant sodium dodecyl sulphate. Previous experiments had shown that the addition of croscarmellose sodium, more lactose or the use of larger capsules did not result in increased dissolution rates of the capsule formulation. Again, this shows that with a surfactant like SDS maximum dissolution is achieved in about 10-15 minutes.

3.3: Addition of Sodium Dodecyl Sulphate to the Solid Dispersion Formulation

In this experiment, the effect on solubility of adding SDS to the solid dispersion was determined.

Paclitaxel 40% Solid Dispersion in PVP-K17

A solid dispersion was prepared by dissolving 600 mg of Paclitaxel in 60 mL t-butanol and 900 mg PVP-K17 in 40 mL water. The paclitaxel/t-butanol solution was added to the PVP-K17/water solution under constant stirring. The final mixture was transferred to 8 mL vials with a maximum fill level of 2 mL. t-butanol and water were subsequently removed by lyophilisation (see table 3).

Paclitaxel 40% Solid Dispersion in PVP-K17 and Sodium Dodecyl Sulphate 10%

A solid dispersion was prepared by dissolving 250 mg of Paclitaxel in 25 mL t-Butanol, and 375 mg PVP-K17 and 62.5 mg sodium dodecyl sulphate (SDS) in 16.67 mL water. The paclitaxel/t-butanol solution was added to the PVP-K17/sodium dodecyl sulphate/water solution under constant stirring. The final mixture was transferred to 8 mL vials with a maximum fill level of 2 mL. t-butanol and water were subsequently removed by lyophilisation (see table 3).

25 mg Paclitaxel Capsules of Paclitaxel/PVP-K17 Solid Dispersion 62.5 mg of a paclitaxel 40%/PVP-K17 solid dispersion (=25 mg paclitaxel) was mixed with 160 mg lactose, 30 mg sodium dodecyl sulphate and 10 mg croscarmellose sodium. The resulting powder mixture was encapsulated (see table 9).

TABLE 9 formulation of 25 mg paclitaxel/PVP-K17 solid dispersion capsules

| Component | Amount (mg) |
| --- | --- |
| paclitaxel (inside the solid dispersion) | 25 mg |
| PVP-K17 (inside the solid dispersion) | 37.5 mg |
| Lactose monohydrate | 125 mg |
| sodium dodecyl sulphate | 30 mg |
| croscarmellose sodium | 10 mg |

25 mg Paclitaxel Capsules of Paclitaxel/PVP-K17/Sodium Dodecyl Sulphate Solid Dispersion 68.75 mg of a paclitaxel 40%/PVP-K17/sodium dodecyl sulphate 10% solid dispersion (=25 mg paclitaxel) was mixed with 160 mg lactose and 10 mg croscarmellose sodium. The resulting powder mixture was encapsulated (see table 10).

TABLE 10 formulation of 25 mg paclitaxel/PVP-K17 solid dispersion capsules

| Component | Amount (mg) |
| --- | --- |
| paclitaxel (inside the solid dispersion) | 25 mg |
| PVP-K17 (inside the solid dispersion) | 37.5 mg |
| sodium dodecyl sulphate (inside the solid dispersion) | 6.25 mg |
| Lactose monohydrate | 125 mg |
| croscarmellose sodium | 10 mg |

Dissolution Test

Both capsule formulations were tested in 500 mL of Water for Injection maintained at 37° C. in a USP 2 (paddle) dissolution apparatus. Rotation speed was set at 75 rpm for the capsule with paclitaxel/PVP-K17/sodium dodecyl sulphate solid dispersion and at 100 rpm for the capsule with paclitaxel/PVP-K17 solid dispersion. Samples were collected at various timepoints and analyzed by HPLC-UV (see table 6).

Results and Conclusions

Figure 7:
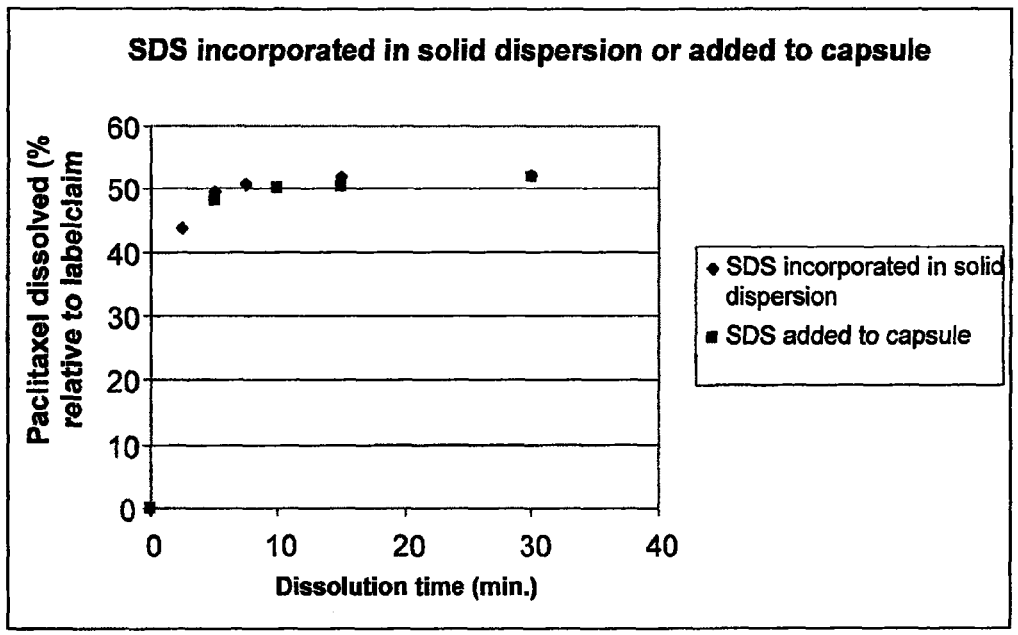
FIG. 7 shows the results of a dissolution test of paclitaxel solid dispersions with sodium dodecyl sulphate incorporated in the solid dispersion or added to the capsule (conditions: 500 mL WfI, 37° C., 75 rpm (100 rpm for SDS added to the capsules))

The results are shown in FIG. 7. The amount of paclitaxel dissolved is expressed relative to the label claim (in this case 25 mg). It can clearly be seen that the dissolution of paclitaxel from capsules with sodium dodecyl sulphate incorporated in the solid dispersion is comparable to the dissolution of paclitaxel from capsules with sodium dodecyl sulphate added to the capsule. Furthermore only 6.25 mg sodium dodecyl sulphate was used for incorporation into the solid dispersion, while 30 mg sodium dodecyl sulphate was used as addition to the capsule formulation. This shows that less surfactant is required when it is incorporated into the solid dispersion rather than into the capsule in order to achieve the similar results. Another surprising result from this experiment is that both compositions provide an absolute paclitaxel solubility of about 26 μg/ml and this level is reached in 20-30 minutes. This result provides a higher solubility and faster dissolution rate than has previously been achieved.

3.4: Influence of Carrier

The solid dispersions used in the experiments of example 3.4 were produced after initial experiments did not show clear differences between drugloads. The 40% drugload was selected because these formulations performed equally to 20% drugload formulation in the afore mentioned experiments and offered the possibility to deliver more taxane in one tablet or capsule.

Paclitaxel 40% Solid Dispersion in PVP-K12

A solid dispersion was prepared by dissolving 250 mg of paclitaxel in 25 mL t-butanol and 375 mg PVP-K12 in 16.67 mL water. The paclitaxel/t-butanol solution was added to the PVP-K12 water solution under constant stirring. The final mixture was transferred to 8 mL vials with a maximum fill level of 2 mL. t-butanol and water were subsequently removed by lyophilisation (see table 3).

Paclitaxel 40% Solid Dispersion in PVP-K17

A solid dispersion was prepared by dissolving 600 mg of paclitaxel in 60 mL t-butanol and 900 mg PVP-K17 in 40 mL water. The paclitaxel/t-butanol solution was added to the PVP-K17 water solution under constant stirring. The final mixture was transferred to 8 mL vials with a maximum fill level of 2 mL. t-butanol and water were subsequently removed by lyophilisation (see table 3).

Paclitaxel 40% Solid Dispersion in PVP-K30

A solid dispersion was prepared by dissolving 250 mg of paclitaxel in 25 mL t-Butanol and 375 mg PVP-K30 in 16.67 mL water. The paclitaxel/t-butanol solution was added to the PVP-K30 water solution under constant stirring. The final mixture was transferred to 8 mL vials with a maximum fill level of 2 mL. t-butanol and water were subsequently removed by lyophilisation (see table 3).

Paclitaxel 40% Solid Dispersion in HP-Cyclodextrin

A solid dispersion was prepared by dissolving 250 mg of paclitaxel in 25 mL t-butanol and 375 mg HP-cyclodextrin in 16.67 mL water. The paclitaxel/t-butanol solution was added to the HP-cyclodextrin water solution under constant stirring. The final mixture was transferred to 8 mL vials with a maximum fill level of 2 mL. t-butanol and water were subsequently removed by lyophilisation (see table 3).

25 mg Paclitaxel Solid Dispersion Capsules 62.5 mg of the paclitaxel/carrier solid dispersion (=25 mg paclitaxel) was mixed with 160 mg Lactose, 30 mg sodium dodecyl sulphate and 10 mg croscarmellose sodium. The resulting powder mixture was encapsulated (see table 11).

TABLE 11 formulation of 25 mg paclitaxel/carrier solid dispersion capsules

| Component | Amount (mg) |
|---|---|
| paclitaxel (inside the solid dispersion) | 25 mg |
| carrier (inside the solid dispersion) | 37.5 mg |
| Lactose monohydrate | 125 mg |
| sodium dodecyl sulphate | 30 mg |
| croscarmellose sodium | 10 mg |

Dissolution Test

All capsule formulations were tested in 500 mL of Water for Injection maintained at 37° C. in a USP 2 (paddle) dissolution apparatus with a rotation speed of 100 rpm. Samples were collected at various timepoints and analyzed by HPLC-UV (see table 6).

Results and Conclusions

Figure 8:
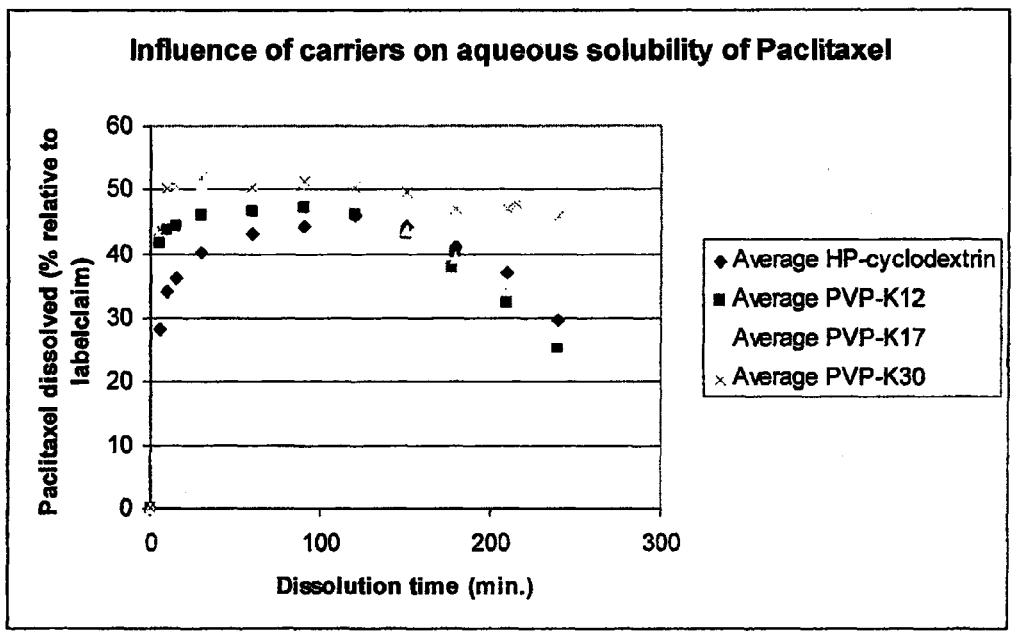
FIG. 8 shows the results of a dissolution test of paclitaxel solid dispersions with various carriers (conditions: 500 mL WfI, 37° C., 100 rpm)

The average results of 2 to 3 experiments are shown in FIG. 8. The amount of paclitaxel dissolved is expressed relative to the label claim (in this case 25 mg). It can clearly be seen that the dissolution of paclitaxel from the PVP-K30 solid dispersion is as fast as the dissolution of paclitaxel from the PVP-K17 solid dispersion. However, the amount of paclitaxel dissolved remains higher throughout the 4 hour experiment in the case of the PVP-K30 solid dispersion.

The chain length of the polymeric carrier determines the time to crystallization in aqueous environments.

3.5: Influence of Drug/Carrier Ratio

The solid dispersions used in the experiments of example 3.5 were produced after initial experiments did not show clear differences between carriers. These initial experiments were done before the more detailed experiments of Example 3.4. As a result, PVP-K17 was arbitrarily chosen as carrier for further experiments.

Paclitaxel 10% Solid Dispersion in PVP-K17

A solid dispersion was prepared by dissolving 100 mg of paclitaxel in 10 mL t-butanol and 900 mg PVP-K17 in 40 mL water. The paclitaxel/t-butanol solution was added to the PVP-K17 water solution under constant stirring. The final mixture was transferred to 8 mL vials with a maximum fill level of 2 mL. t-butanol and water were subsequently removed by lyophilisation (see table 3).

Paclitaxel 25% Solid Dispersion in PVP-K17

A solid dispersion was prepared by dissolving 250 mg of paclitaxel in 25 mL t-butanol and 750 mg PVP-K17 in 16.67 mL water. The paclitaxel/t-butanol solution was added to the PVP-K17 water solution under constant stirring. The final mixture was transferred to 8 mL vials with a maximum fill level of 2 mL. t-butanol and water were subsequently removed by lyophilisation (see table 3).

Paclitaxel 40% Solid Dispersion in PVP-K17

A solid dispersion was prepared by dissolving 600 mg of paclitaxel in 60 mL t-butanol and 900 mg PVP-K17 in 6.67 mL water. The paclitaxel/t-butanol solution was added to the PVP-K17 water solution under constant stirring. The final mixture was transferred to 8 mL vials with a maximum fill level of 2 mL. t-butanol and water were subsequently removed by lyophilisation (see table 3).

Paclitaxel 75% Solid Dispersion in PVP-K17

A solid dispersion was prepared by dissolving 250 mg of paclitaxel in 25 mL t-butanol and 83 mg PVP-K17 in 16.67 mL water. The paclitaxel/t-butanol solution was added to the PVP-K17 water solution under constant stirring. The final mixture was transferred to 8 mL vials with a maximum fill level of 2 mL. t-butanol and water were subsequently removed by lyophilisation (see table 3).

Paclitaxel 100% Solid Dispersion

A solid dispersion was prepared by dissolving 250 mg of paclitaxel in 25 mL t-butanol. The paclitaxel/t-butanol solution was added to 16.67 mL water under constant stirring. The final mixture was transferred to 8 mL vials with a maximum fill level of 2 mL. t-butanol and water were subsequently removed by lyophilisation (see table 3).

Dissolution Test

An amount of solid dispersion powder, equal to approximately 4 mg Paclitaxel, was placed in a 50 mL beaker. A magnetic stirring bar and 25 mL water was added to the beaker. The solution was stirred at 7200 rpm. Samples were collected at various timepoints and analyzed by HPLC-UV (see table 6).

Results and Conclusions

Figure 9:
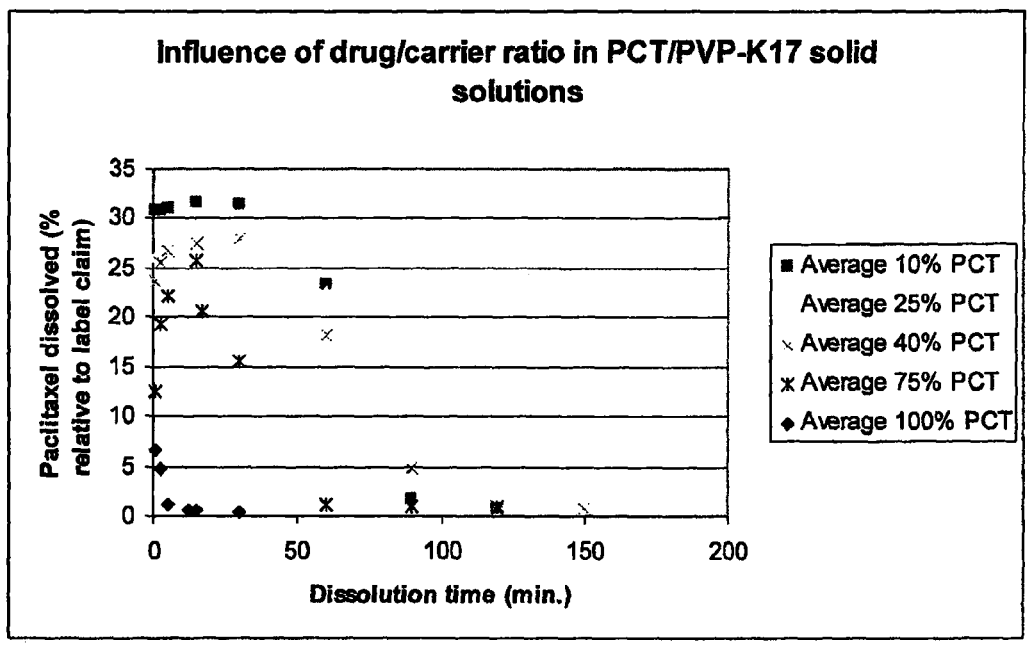
FIG. 9 shows the results of a solubility test of paclitaxel/PVP-K17 solid dispersions with various drug-carrier ratios (conditions: 25 mL WfI, 37° C., 7200 rpm)

The average results of 2 to 3 experiments are shown in FIG. 9. The amount of paclitaxel (PCT) dissolved is expressed relative to the label claim (in this case approximately 4 mg). The influence of the drug/carrier ratio is immediately apparent from FIG. 9. The value of the peak concentration of paclitaxel inversely related to the drug/carrier ratio. The highest peak concentration is reached with the lowest drug/carrier ratio (10%), while the lowest peak concentration is reached with the highest drug/carrier ratio (100%). Furthermore, the AUC-values of the 10% drug/carrier ratio solid dispersion are the highest, followed by the AUC-values of 25, 40, 75 and 100% drug/carrier ratio solid dispersions.

The amount of carrier relative to the amount of drug determines the time to crystallization in aqueous environments.

3.6: Influence of Enteric Coating

Paclitaxel 40% Solid Dispersion in PVP-K17 and Sodium Dodecyl Sulphate 10%

A solid dispersion was prepared by dissolving 250 mg of paclitaxel in 25 mL t-butanol, and 375 mg PVP-K17 and 62.5 mg sodium dodecyl sulphate (SDS) in 16.67 mL water. The paclitaxel/t-butanol solution was added to the PVP-K17/sodium dodecyl sulphate/water solution under constant stirring. The final mixture was transferred to 8 mL vials with a maximum fill level of 2 mL. t-butanol and water were subsequently removed by lyophilisation (see table 3).

25 mg Paclitaxel Capsules of Paclitaxel/PVP-k17/Sodium Dodecyl Sulphate Solid Dispersion 68.75 mg of a paclitaxel 20%/PVP-K17/sodium dodecyl sulphate 10% solid dispersion (=25 mg paclitaxel) was mixed with 160 mg lactose and 10 mg croscarmellose sodium. The resulting powder mixture was encapsulated (see table 12).

TABLE 12 formulation of 25 mg paclitaxel/PVP-K17/SDS solid dispersion capsules

| Component | Amount (mg) |
|---|---|
| paclitaxel (inside the solid dispersion) | 25 mg |
| PVP-K17 (inside the solid dispersion) | 37.5 mg |
| sodium dodecyl sulphate (inside the solid dispersion) | 6.25 mg |
| Lactose monohydrate | 125 mg |
| croscarmellose sodium | 10 mg |

Dissolution Test

The capsules were in duplo subjected to two different dissolution tests. The first test was a two tiered dissolution test, consisting of two hours of dissolution testing in 500 mL simulated gastric fluid without pepsin ($SGF_{sp}$; see table 13) followed by two hours of dissolution testing in 629 mL simulated intestinal fluid without pepsin ($SIF_{sp}$; see table 13). The second test was conducted in 500 mL fasted state simulated intestinal fluid (FaSSIF; see table 14) medium for four hours.

Both dissolution tests were performed in a USP 2 (paddle) dissolution apparatus with 500 mL medium maintained at 37° C. and paddle rotation speed 75 rpm. The SGFsp medium was changed to SIFsp medium by addition of 129 mL switch medium. Samples were collected at various timepoints and analyzed by HPLC-UV (see table 6).

TABLE 13

$SGF_{sp}$, $SIF_{sp}$ and switch medium [96]

| Medium | Volume | Components |
|---|---|---|
| $SGF_{sp}$ (USP 26) | 500 mL | 1.0 g NaCL, 3.5 mL HCl, q.s. 500 mL Water for Injection |
| Switch medium | 129 mL | 4.08 g KH$_2$PO4, 30 mL NaOH solution 80 g/L (2.0 M), 129 mL Water for Injection |
| $SIF_{sp}$ + NaCL (USP 24) | 629 ML | 500 mL $SGF_{sp}$ and 129 mL switch medium |

TABLE 14

Fasted state simulated intestinal fluid (FaSSIF) medium [97]

| Component | Amount |
|---|---|
| KH$_2$PO4 | 3.9 g |
| NaOH | q.s. pH 6.5 |
| Na taurocholate | 3 mM |
| Lecithin | 0.75 mM |
| KCl | 7.7 g |
| Distilled water | q.s. 1 L |

Results and Conclusions

Figure 10:
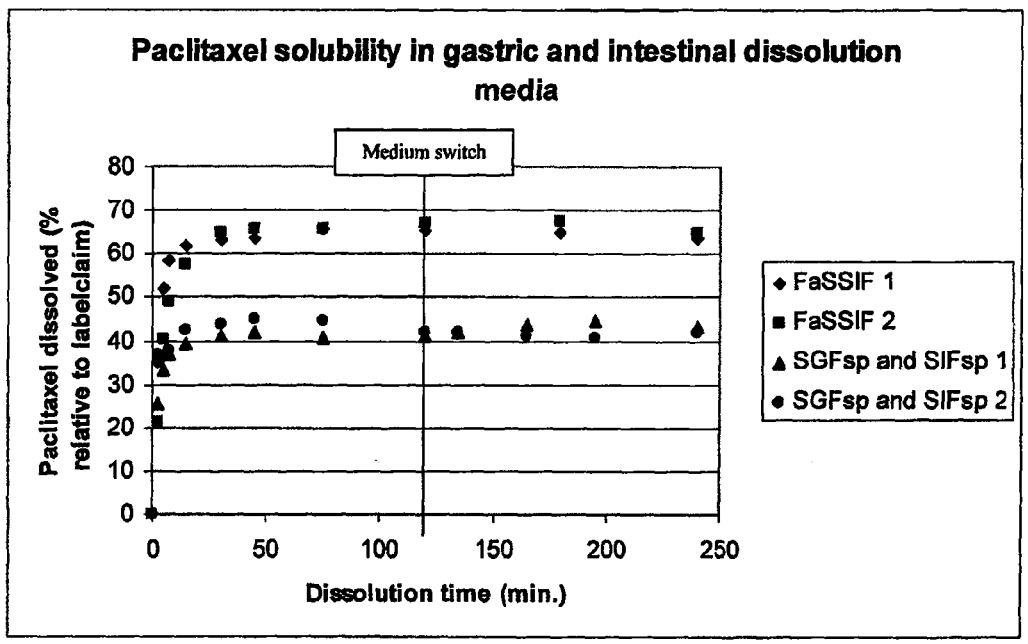
FIG. 10 shows the results of a dissolution test of paclitaxel solid dispersions in various media (conditions: 500 mL FaSSIF (light grey), 37° C., 75 rpm; or 500 mL SGF$_{sp}$ and 629 mL SIF$_{sp}$, 37° C., 75 rpm (dark grey))

The results are shown in FIG. 10. The amount of paclitaxel dissolved is expressed relative to the label claim (in this case 25 mg). Paclitaxel dissolution in Fasted state simulated intestinal fluid is approximately 20% higher than in simulated gastric fluid (SGFsp). After two hours in SGFsp the amount of paclitaxel in solution is only slightly increased when the medium is changed to simulated intestinal fluid (SIFsp).

An enteric coating will prevent release of the taxane in the stomach, thereby preventing degradation of the active components. Furthermore, it will enable targeted delivery to the intestines where the taxane is absorbed, thus ensuring that the limited time the taxane is present in solution (before crystallization takes place), is only spent at sites where absorption is possible.

Example 4

Oral Formulations of Docetaxel

Materials and Methods

The formulations used in the following experiments were prepared according to the procedures outline below and the compositions depicted in table 15.

Pure Anhydrous Docetaxel

Anhydrous docetaxel was used as obtained from ScinoPharm, Taiwan.

Pure Amorphous Docetaxel

Docetaxel was amorphized by dissolving 300 mg of Docetaxel anhydrate in 30 mL of t-butanol. The docetaxel/t-butanol solution was added to 20 mL of Water for Injection (WfI) under constant stirring. The final mixture was transferred to a stainless steel lyophilisation box (Gastronorm size 1/9), t-butanol and water were subsequently removed by lyophilisation (see table 16).

Physical Mixtures

Physical mixtures were prepared by mixing 150 mg of docetaxel and corresponding amounts of carrier and surfactant (see table 15) with mortar and pestle.

Solid Dispersions

Solid dispersions were obtained by dissolving 300 mg docetaxel anhydrate in 30 mL of t-butanol, and corresponding amounts of carrier and surfactant (see table 15) in 20 mL of Water for Injection. The docetaxel/t-butanol solution was added to the carrier/surfactant/WfI solution under constant stirring. The final mixture was transferred to a stainless steel lyophilisation box (Gastronorm size 1/9), t-butanol and water were subsequently removed by lyophilisation (see table 16).

TABLE 15

Composition of the tested formulations

| Formulation | Type | Drug | Part | Amount (mg) | Carrier | Part | Amount (mg) | Surfactant | Amount (mg) | Part |
|---|---|---|---|---|---|---|---|---|---|---|
| A | Pure drug | Anhydrous Docetaxel | 1 | 150 | — | — | — | — | — | — |
| B | Pure drug | Amorphous Docetaxel | 1 | 450 | — | — | — | — | — | — |
| C | Physical mixture | Anhydrous Docetaxel | 1/11 | 150 | PVP-K30 | 9/11 | 1350 | SDS | 150 | 1/11 |
| D | Physical mixture | Amorphous Docetaxel | 1/11 | 150 | PVP-K30 | 9/11 | 1350 | SDS | 150 | 1/11 |
| E | Solid dispersion | Amorphous Docetaxel | 1/11 | 300 | PVP-K30 | 9/11 | 2700 | SDS | 300 | 1/11 |
| F | Solid dispersion | Amorphous Docetaxel | 1/11 | 300 | HPβ-CD[1] | 9/11 | 2700 | SDS | 300 | 1/11 |
| G | Solid dispersion | Amorphous Docetaxel | 1/11 | 300 | PVP-K12 | 9/11 | 2700 | SDS | 300 | 1/11 |
| H | Solid dispersion | Amorphous Docetaxel | 1/11 | 300 | PVP-K17 | 9/11 | 2700 | SDS | 300 | 1/11 |
| I | Solid dispersion | Amorphous Docetaxel | 1/11 | 300 | PVP-K25 | 9/11 | 2700 | SDS | 300 | 1/11 |
| J | Solid dispersion | Amorphous Docetaxel | 1/11 | 300 | PVP-K90 | 9/11 | 2700 | SDS | 300 | 1/11 |
| K | Solid dispersion | Amorphous Docetaxel | 5/7 | 300 | PVP-K30 | 5/21 | 100 | SDS | 20 | 1/21 |
| L | Solid dispersion | Amorphous Docetaxel | 1/3 | 300 | PVP-K30 | 1/2 | 450 | SDS | 150 | 1/6 |
| M | Solid dispersion | Amorphous Docetaxel | 1/6 | 300 | PVP-K30 | 2/3 | 1200 | SDS | 300 | 1/6 |
| N | Solid dispersion | Amorphous Docetaxel | 1/21 | 300 | PVP-K30 | 19/21 | 5700 | SDS | 300 | 1/21 |

[1]HPβ-CD is hydroxypropyl-β-cyclodextrin

TABLE 16 lyophilisation conditions

| Step | Time (hh:mm) | Shelve temperature (° C.) | Room pressure (mbar) | Maximum pressure (mbar) |
|---|---|---|---|---|
| 1 | 00:00 | Ambient | 1000 | 1000 |
| 2 | 01:00 | −35 | 1000 | 1000 |

TABLE 16-continued

| | | lyophilisation conditions | | |
|---|---|---|---|---|
| Step | Time (hh:mm) | Shelve temperature (° C.) | Room pressure (mbar) | Maximum pressure (mbar) |
| 3 | 03:00 | −35 | 1000 | 1000 |
| 4 | 03:01 | −35 | 0.2 | 0.6 |
| 5 | 48:00 | −35 | 0.2 | 0.6 |
| 6 | 63:00 | 25 | 0.2 | 0.6 |
| 7 | 66:00 | 25 | 0.2 | 0.6 |

Dissolution Test

An amount of powder, equal to approximately 6 mg Docetaxel, was placed in a 50 mL beaker. A magnetic stirring bar and 25 mL water were added to the beaker. The solution was stirred at 720 rpm, and kept at approximately 37° C. Samples were collected at various timepoints, and filtrated using a 0.45 μm filter before they were diluted with a 1:4 v/v mixture of methanol and acetonitrile. The filtrated and diluted samples were subsequently analyzed by HPLC-UV (see table 17).

TABLE 17

| chromatographic conditions | |
|---|---|
| Column | Apex octyl 150 × 4.6 mm 5 μm |
| Eluens | Methanol/Acetonitrile/0.02 M Ammoniumacetate 1/4/5 v/v/v |
| Flow | 1.0 mL/min |
| Injection volume | 10 μL |
| Run time | 20 minutes |
| Detection wavelength | 227 nm |

4.1: Formulation Type

In the first experiment, the influence of the formulation type on the solubility of docetaxel was examined. Data from the dissolution test performed on formulations A to E were compared. The results are shown in FIG. 11. Formulation E was tested in quadruplicate, formulation A to D were tested in duplicate.

Results

Formulation A (pure docetaxel anhydrate) reaches a maximum concentration of approximately 12 μg/mL (4.7% total docetaxel present) after 5 minutes of stirring and reaches an equilibrium concentration of approximately 6 μg/mL (2%) after 15 minutes of stirring.

Formulation B (pure amorphous docetaxel) reaches a maximum of 32 μg/mL (13%) after 0.5 minutes, from 10 to 60 minutes the solubility is comparable to formulation A.

Formulation C (physical mixture of anhydrous docetaxel, PVP-K30 and SDS) reaches a concentration of approximately 85 μg/mL (37%) after 5 minutes. Between 15 and 25 minutes, the docetaxel concentration sharply declines from 85 μg/mL (37%) to 30 μg/mL (12%), after which it further declines to 20 μg/mL (9%) at 60 minutes.

Formulation D (physical mixture of amorphous docetaxel, PVP-K30 and SDS) reaches a maximum docetaxel concentration of 172 μg/mL (70%) after 7.5 minutes. Between 7.5 and 20 minutes, the amount of docetaxel in solution drops to 24 μg/mL (10%). At 60 minutes, the equilibrium concentration of 19 μg/mL (7%) is reached.

Formulation E (solid dispersion of amorphous docetaxel, PVP-K30 and SDS) has the highest maximum concentration of 213 μg/mL (900%) which is reached after 5 minutes. Between 10 and 25 minutes, the amount of docetaxel in solution rapidly declines resulting in an equilibrium concentration of 20 μg/mL (8%) after 45 minutes.

Conclusions

All formulations initially show a higher solubility, which decreases to an equilibrium solubility after 45 to 60 minutes of stirring. The decrease in solubility is caused by the crystallization of docetaxel as a result of the supersaturated solution. The degree of supersaturation is dependent on the physical state of the drug, i.e. whether it is amorphous or crystalline. When PVP-K30 is the carrier, the supersaturated state is maintained for longer so that the solubility of the docetaxel does not decrease as quickly. Further, the results show that using amorphous docetaxel significantly increases the solubility of docetaxel compared to anhydrous docetaxel. Further, amorphous docetaxel shows a relatively high dissolution rate, peaking at about 5 to 7.5 minutes.

This experiment shows that the amount of docetaxel in solution is markedly increased by physical mixing of anhydrous docetaxel with PVP-K30 and SDS, and even more by physical mixing of amorphous docetaxel with PVP-K30 and SDS. The biggest increase in solubility however is achieved by incorporation of docetaxel in a solid dispersion of PVP-K30 and SDS.

4.2: Carrier Type

In the second experiment, the influence of the carrier type on the solubility of docetaxel was examined. Data from the dissolution test performed on formulation E and F were compared. The results are shown in FIG. 12. Formulation E was tested in quadruplicate, formulation F was tested in duplicate.

Results

Formulation E (solid dispersion of amorphous docetaxel, PVP-K30 and SDS) has a highest maximum concentration of 213 μg/mL (90% of total docetaxel present) which is reached after 5 minutes. Between 10 and 25 minutes, the amount of docetaxel in solution rapidly declines, resulting in an equilibrium concentration of 20 μg/mL (8%) after 45 minutes.

Formulation F (solid dispersion of amorphous docetaxel, HPβ-CD and SDS) reaches a maximum docetaxel concentration of approximately 200 μg/mL (81%) after about 2 minutes. Between 5 and 10 minutes, the amount of docetaxel in solution drops to a value of 16 μg/mL (6%) and after 45 minutes, an equilibrium concentration of 11 μg/mL (4%) is reached.

Conclusions

This experiment shows that both PVP-K30 and HPβ-CD increase the solubility of docetaxel. When PVP-K30 is used as the carrier compared to HPβ-CD, the maximum docetaxel concentration is slightly higher and the state of supersaturation is maintained longer so that the solubility of docetaxel does not decrease as quickly with time. Further, the equilibrium concentration reached after precipitation of docetaxel is higher with PVP-K30 compared to HPβ-CD.

4.3: Chain Length

In the third experiment, the influence of the PVP chain length on the solubility of docetaxel was examined. Data of the dissolution test performed on formulation E and G to J were compared. The results are shown in FIG. 13. Formulation E was tested in quadruplicate, formulation G to J were tested in duplicate.

Results

Formulation G (PVP-K12) reaches a maximum docetaxel concentration of 206 μg/mL (77% of the total docetaxel present) after 5 minutes. Between 5 and 30 minutes, the amount of docetaxel in solution decreases to 20 μg/mL (7%) and at 45 minutes, the docetaxel concentration is 17 μg/mL (6%).

Formulation H (PVP-K17) reaches a maximum docetaxel concentration of 200 μg/mL (83%) after 5 minutes and maintains this concentration up to 10 minutes of stirring, after which the amount of docetaxel in solution rapidly drops to 44 µg/mL (18%) at 15 minutes and 22 µg/mL (9%) at 30 minutes. The equilibrium concentration between 45 and 60 minutes is approximately 21 µg/mL (8%).

Formulation I (PVP-K25) reaches a maximum docetaxel concentration of 214 µg/mL (88%) after 5 minutes of stirring. The amount of docetaxel in solution decreases between 10 and 30 minutes to 22 µg/mL (9%) and at 60 minutes, the concentration of docetaxel is 19 µg/mL (8%).

Formulation E (PVP-K30) has a maximum docetaxel concentration of 213 µg/mL (90%) which is reached after 5 minutes. Between 10 and 25 minutes, the amount of docetaxel in solution rapidly declines, resulting in an equilibrium concentration of 20 µg/mL (8%) after 45 minutes.

Formulation J (PVP-K90) reaches a maximum docetaxel concentration of 214 µg/mL (88%) after 10 minutes of stirring. At 15 minutes, the amount of docetaxel in solution is still 151 µg/mL (61%). After 60 minutes, the docetaxel concentration has declined to 19 µg/mL (7%).

Conclusions

This experiment shows that the chain length of PVP influences both the degree of supersaturation and the period the supersaturation is maintained. The use of higher PVP chain lengths results in a higher maximum docetaxel concentrations and a longer period of supersaturation, thus, a higher solubility for a longer period of time.

4.4: Drug Load

In the fourth experiment, the influence of the drug load on the solubility of docetaxel was examined. Data from the dissolution tests performed on formulations E and K to N were compared. The results are shown in FIG. 14. Formulation E was tested in quadruplicate, formulation K to N were tested in duplicate.

Formulation N (1/21 docetaxel by weight of total composition; 5:95 w/w docetaxel to PVP) reaches a maximum docetaxel concentration of 197 µg/mL (79% of total docetaxel present) after 10 minutes. After 15 minutes, the amount of docetaxel in solution is still 120 µg/mL (48%) and between 15 and 30 minutes, the docetaxel concentration decreases to 24 µg/mL (12%). At 60 minutes the docetaxel concentration is 20 µg/mL (8%).

Formulation E (1/11 docetaxel by weight of total composition; 10:90 w/w docetaxel to PVP) has a maximum concentration of 213 µg/mL (90%) which is reached after 5 minutes. Between 10 and 30 minutes, the amount of docetaxel in solution rapidly declines and reaches an equilibrium concentration of 20 µg/mL (8%) after 45 minutes.

Formulation M (1/6 docetaxel by weight of total composition; 20:80 w/w docetaxel to PVP) has a docetaxel concentration of 196 µg/mL (80%) after 10 minutes of stirring. The amount of docetaxel in solution decreases between 10 and 30 minutes to 25 µg/mL (10%) and at 60 minutes, the concentration of docetaxel is 18 µg/mL (7%).

Formulation L (1/3 docetaxel by weight of total composition; 40:60 w/w docetaxel to PVP) reaches a docetaxel concentration of 176 µg/mL (71%). Between 10 and 15 minutes, the amount of docetaxel in solution rapidly drops to 46 µg/mL (18%) and after 60 minutes, the amount of docetaxel in solution is 18 µg/mL (7%).

Formulation K (5/7 docetaxel by weight of total composition; 75:25 w/w docetaxel to PVP) reaches a maximum docetaxel value of 172 µg/mL (71%) after 5 minutes of stirring. Between 5 and 10 minutes, the docetaxel concentration sharply declines to 42 µg/mL (17%) and after 60 minutes, a docetaxel concentration of 18 µg/mL (7%) is reached.

Conclusions

This experiment shows that the amount of PVP-K30 relative to the amount of docetaxel used in the solid dispersions influences both the degree of supersaturation and the period the supersaturation is maintained. The use of higher drug-loads results in lower maximum docetaxel concentrations and a shorter period of supersaturation, thus, a lower solubility over time.

4.5: Solubility Comparison with a Prior Art Composition

In this experiment, a composition containing a solid dispersion of 15 mg docetaxel, 135 mg PVP-K30 and 15 mg SDS was compared to a the literature data of a composition comprising a solid dispersion of 5 mg docetaxel and PVP-K30 as disclosed in Chen et al. [95]. The solubility results were obtained using the dissolution test described in Chen et al. [95] and are shown in FIGS. 15 and 16. A dissolution test was also conducted in Simulated Intestinal Fluid and compared to the literature data of Chen. The results are shown in FIG. 17.

Results

From FIG. 15, it can be seen that the composition of Chen et al. can dissolve a maximum of about 80% of the 5 mg docetaxel in the composition in 900 ml water. It took over 5 hours to reach this maximum. The docetaxel, PVP-K30 and SDS composition dissolved 100% of the 15 mg docetaxel in about 60 minutes.

In FIG. 16, the absolute concentration of docetaxel is given. The composition of Chen gave a maximum docetaxel concentration of about 4.2 µg/ml after about 5 hours. The docetaxel, PVP-K30 and SDS composition gave a maximum docetaxel concentration of about 16.7 µg/ml after about 60 minutes.

In FIG. 17, the docetaxel capsules reach a solubility of 28 µg/ml (>90% solubility). The solid dispersion described by Chen et al. (docetaxel+PVP K30) reaches a solubility of 4.2 µg/ml (lower than 80% of the 5 mg docetaxel solid dispersion tested for dissolution in 900 ml). The capsule formulation thus reaches a 6.6 fold better solubility with a higher dissolution rate (maximum reached after 30 minutes versus 90-120 minutes by Chen).

Conclusions

From these results, it can be seen that the docetaxel, PVP-K30 and SDS composition gave a faster dissolution rate and a higher solubility compared to the composition of Chen. For bioavailability, it is important to look at how fast a drug dissolves and what solubility is reached in 0.5 to 1.5 h.

From the results of Chen, a skilled person would not consider that increasing the amount of docetaxel in the composition would increase the absolute solubility of docetaxel. Since the composition of Chen dissolves only 80% of 5 mg docetaxel (i.e. 4 mg) in 900 ml water, you would not expect that increasing the amount of docetaxel to 15 mg would cause any more than 4 mg docetaxel to dissolve. Thus, you would expect a 15 mg docetaxel composition according to Chen to dissolve a maximum of about 27% docetaxel compared to 100% for the docetaxel, PVP-K30 and SDS composition. Therefore, the docetaxel, PVP-K30 and SDS composition provides surprisingly good results compared to Chen.

4.6: Dissolution Test in Simulated Intestinal Fluid sine Pancreatin (SIFsp)

In this experiment, the dissolution of capsules, containing a solid dispersion of docetaxel, PVP-K30 and SDS, was tested in Simulated Intestinal Fluid sine Pancreatin (SIFsp). The capsules contained 15 mg docetaxel according to Formulation E (see table 15). SIFsp was prepared according to USP 28. Capsules containing 15 mg docetaxel were dissolved in 500 mL USP SIFsp at 37° C. with stirring at 75 rpm. The results are shown in FIGS. 18 and 19.

FIGS. 18 and 19 show that nearly 100% of the docetaxel dissolved. This is equivalent to an absolute docetaxel concentration of about 29 μg/ml and is achieved in about 30 minutes. Thus, the composition provides a relatively high solubility in a relatively short period of time.

4.7: Stability

It was found that the solid dispersion of docetaxel, PVP-K30 and SDS according to Formulation E (see table 15) and which was used in capsules for clinical trials (see following Example) is stable both chemically (no degradation) and physically (no changes in solubility characteristics) for at least 80 days when stored between 4-8° C.

Example 5

Clinical Trial Data with Formulations

Materials and Methods 10 patients participated in an ongoing clinical phase I trial. These patients were given the following numbers: 301, 302, 303, 304, 305, 306, 307, 308, 309 and 310.

These patients were given medication which consisted of a liquid formulation of docetaxel or a solid composition comprising a solid dispersion of docetaxel, PVP-K30 and SDS (referred to hereinafter as MODRA).

Liquid Formulation

Docetaxel dose: 30 mg for all patients (with the exception of patient 306 who received 20 mg docetaxel). The 30 mg dose was prepared as follows: 3.0 mL Taxotere® premix for intravenous administration (containing 10 mg docetaxel per ml in polysorbate 80 (25% v/v), ethanol (10% (w/w), and water) was mixed with water to a final volume of 25 mL. This solution was orally ingested by the patient with 100 mL tap water.

MODRA

Docetaxel dose: 30 mg; 2 capsules with 15 mg docetaxel per capsule were ingested. Formulation E from the previous example (1/11 docetaxel, 9/11 PVP-K30 and 1/11 SDS) was selected for further testing in the clinical trial. A new batch of formulation E was produced by dissolving 1200 mg docetaxel anhydrate in 120 mL of t-butanol, and 10800 mg PVP-K30 and 1200 mg SDS (see table 15) in 80 mL of Water for Injection. The docetaxel/t-butanol solution was added to the PVP-K30/SDS/WfI solution under constant stirring. The final mixture was transferred to a stainless steel lyophilisation box (Gastronorm size 1/3), t-butanol and water were subsequently removed by lyophilisation (see table. 16).

A total of 60 gelatine capsules of size 0 were filled with an amount of solid dispersion equivalent to 15 mg docetaxel, an HPLC assay was used to determine the exact amount of docetaxel per mg of solid dispersion. The assay confirmed that the capsules contained 15 mg docetaxel.

Patients took the medication orally on an empty stomach in the morning with 100 mL tap water.

Patient Treatment

Patients 301, 302, 303, 304 and 305 received only liquid formulation.

Patient 306 received 20 mg docetaxel as liquid formulation+ritonavir in the first cycle and in the second cycle the same medication but with extra ritonavir 4 hours after docetaxel ingestion.

Patients 307, 308, 309 and 310 received liquid formulation and/or MODRA. Cycles were administered in a weekly interval.

According to institutional guidelines, for both oral and i.v. docetaxel all patients were treated with oral dexamethason. A dose of 4 mg dexamethason was given 1 hour prior to the study drugs, followed by 4 mg every 12 hours (2 times). One hour prior to docetaxel treatment, patients also received 1 mg granisetron (Kytril®) to prevent nausea and vomiting.

After drug administration, blood samples were collected for pharmacokinetic analyses. A blank sample was taken before dosing. Blood samples were centrifuged, plasma was separated and immediately stored at −20° C. until analyses. Analysis were performed with validated HPLC methods in a GLP (Good Laboratory Practice) certified laboratory [101].

Results

Table 18 gives an overview of the individual phamacokinetic results.

| ID | Treatment | Cycle | Tlast(h) I | Conc last | AUC last | AUC inf |
|---|---|---|---|---|---|---|
| 306 | 20 mgdocLF 1x RTV | 1 | 48.03 | 0.668 | 242.7 | 256.5 |
| 306 | 20 mgdocLF 2x RTV | 2 | 48.02 | 1.34 | 357.2 | 384.5 |
| 301 | 30 mg docLF | 2 | 47.78 | 1.42 | 556.7 | 586.5 |
| 302 | 30 mg docLF | 2 | 8.15 | 141 | 2227.1 | 3028.1 |
| 303 | 30 mg docLF | 2 | 48 | 3.28 | 663.9 | 745.4 |
| 304 | 30 mg docLF | 2 | 47.77 | 2.67 | 723.4 | 761.3 |
| 305 | 30 mg docLF | 2 | 48.07 | 0.498 | 129.8 | 140.5 |
| 307 | 30 mg docLF | 3 | 23.9 | 5.17 | 754.3 | 822.0 |
| 309 | 30 mg docLF | 1 | 24.02 | 14.1 | 2127.5 | 2327.0 |
| 310 | 30 mg docLF | 1 | 24.17 | 6.17 | 758.7 | 836.1 |
| 307 | MODRA 30 mg | 1 | 24.07 | 4.23 | 420.8 | 473.8 |
| 307 | MODRA 30 mg | 2 | 23.97 | 7.05 | 782.1 | 873.6 |
| 308 | MODRA 30 mg | 1 | 23.95 | 10.9 | 645.7 | 879.2 |
| 308 | MODRA 30 mg | 2 | 24.02 | 7.76 | 507.3 | 625.9 |
| 309 | MODRA 30 mg | 2 | 23.8 | 7.09 | 892.2 | 994.1 |
| 310 | MODRA 30 mg | 2 | 23.63 | 8.52 | 650.7 | 760.3 | docLF: docetaxel liquid formulation
MODRA: docetaxel capsule formulation
Tlast: time at which last sample for measurement docetaxel concentration was taken (in h)
Conc last: docetaxel concentration at Tlast (in ng/mL)
AUC last: AUC calculated until Conc last (ng · h/mL)
AUC inf: AUClast + extrapolation to infinity (ng · h/mL)
Ritonavir dosage is in all cases 100 mg (capsule, Norvir®)

Patients 301, 302, 303, 304, 305, 307, 309 and 310 received the liquid formulation. The mean, and the 95% confidence interval for the mean of the AUC (extrapolated to infinity) is: 1156 (±348) ng*h/mL. The inter-individual variability is 85%.

Patient 306 received 20 mg docetaxel (as liquid formulation) concomitantly with 100 mg ritonavir in the first cycle and the same combination, one week later, in the second cycle but with 100 mg extra ritonavir 4 hours after ingestion of docetaxel, i.e. two doses of ritonavir were taken, one at t=0 and the second at t=4 h. The pharmacokinetic curves are depicted in FIG. 20.

Patients 307, 308, 309 and 316 received liquid formulation and/or MODRA. The pharmacokinetic curves are depicted in FIG. 21.

FIG. 22 depicts the pharmacokinetic curves of the patients who received the liquid formulation (307, 309 and 310) and all courses (n=6) of the four patients who received MODRA (307, 308, 309 and 310).

The pharmacokinetic results of the liquid formulation versus MODRA, both in combination with 100 mg ritonavir, are summarized below:

Liquid Formulation (30 mg Docetaxel)
$AUC_{inf}$ (95% confidence interval of the mean): 1156 (808–1504) ng*h/ml
Inter-individual variability: 85% (n=8)
MODRA (30 mg Docetaxel)
$AUC_{inf}$ (95% confidence interval of the mean): 768 (568–968) ng*h/ml Inter-individual variability: 29% (n=4)
Intra-individual variability: 33% (n=2)

The average AUC of MODRA was calculated using the 6 curves from four patients. The first dose of MODRA administered to each patient, was used to calculate the inter-individual variability. The intra-individual variability is based on data from patients 307 and 308 who received two doses of MODRA.

Conclusions

The tested docetaxel Liquid Formulation results in an AUC value that is approximately 1.5 fold higher than the same dose (30 mg) given in the novel capsule formulation (MODRA).

The inter-individual variability of the liquid formulation is high (85%) while the inter-individual variability of the capsule formulation is substantially lower (29%). This is an important feature of the novel capsule formulation and provides a much better predictable docetaxel exposure. Also for safety reasons low inter-individual variability is very much desired in oral chemotherapy regimens.

The intra-individual variability (limited data) is in the same order of magnitude as the inter-individual variability.

A second boosting dose of 100 mg ritonavir ingested 4 hours after docetaxel administration increases the docetaxel AUC 1.5 fold.

Comparison of Oral Capsule Formulations Compared to i.v. Administration

FIG. 23 shows pharmacokinetic curves after i.v. (20 mg docetaxel as a i.v. 1-hour infusion, Taxotere®) (n=5 patients) and oral administration of docetaxel (30 mg docetaxel; MODRA capsules, see above) (n=4 patients; 6 courses). Both i.v. and oral docetaxel administration was combined with administration of 100 mg ritonavir (capsule, Norvir®). According to institutional guidelines, for both oral and i.v. docetaxel, all patients were treated with oral dexamethason. A dose of 4 mg dexamethason was given 1 hour prior to the study drugs, followed by 4 mg every 12 hours (2 times). One hour prior to docetaxel treatment, patients also received 1 mg granisetron (Kytril®) to prevent nausea and vomiting.

The bioavailability of the MODRA capsules was calculated by:

$$(AUC\ 30\ mg\ oral/AUC\ 20\ mg\ iv) \times (20/30) \times 100\% = 73\%\ (SD\ 18\%).$$

This shows that the bioavailability of the capsules is relatively high with a low inter-individual variability.

The foregoing Examples are intended to illustrate specific embodiments of the present invention and are not intended to limit the scope thereof, the scope being defined by the appended claims. All documents cited herein are incorporated herein by reference in their entirety.

REFERENCES

1. Demario M D, Ratain M J. Oral chemotherapy: rationale and future directions. J Clin Oncol 1998; 16:2557-2567.
2. Liu G, Franssen E, Fitch M I et al. Patient preferences for oral versus intravenous palliative therapy. J Clin Oncol 1997; 15:110-115.
3. Meerum Terwogt J M, Beijnen J H, ten Bokkel Huinink W W et al. Co-administration of cyclosporin A enables oral therapy with paclitaxel. Lancet 1998; 352:285.
4. Sparreboom A, van Asperen J, Mayer U et al. Limited oral bioavailability and active epithelial excretion of paclitaxel caused by P-glycoprotein in the intestine. Proc Natl Acad Sci USA 1997; 94:2031-2035.
5. Kuhn J, Rizzo J, Eckhardt J et al. Phase I bioavailability study of oral topotecan. Proc Am Soc Clin Oncol 1995; 14:474.
6. Schellens J H M, Creemers G J, Beijnen J H et al. Bioavailability and pharmacokinetics of oral topotecan: a new topoisomerase inhibitor. Br J Cancer 1996; 73:1268-1271.
7. Hellriegel E T, Bjornnson T D, Hauck W W. Interpatient variability in bioavailability is related to the extent of absorption: implications for bioavailability and bioequivalence studies. Clin Pharmacol Ther 1996; 60:601-607.
8. Huizing M T, Giaccone G, van Warmerdam L J C et al. Pharmacokinetics of paclitaxel and carboplatin in a dose-escalating and sequencing study in patients with non-small cell lung cancer. J Clin Oncol 1997; 15:317-329.
9. Van Asperen J, van Tellingen O, Beijnen J H et al. The pharmacological role of P-glycoprotein in the intestinal epithelium. Pharmacol Res 1998; 37:429-435.
10. Thiebaut F, Tsuruo T, Hamada H et al. Cellular localization of the multidrug-resistance gene product P-glycoprotein in normal human tissues. Proc Natl Acad Sci USA 1987; 84:7735-7738.
11. Fojo A T, Ueda K, Slamon D J et al. Expression of a multidrug resistance gene in human tumours and tissues. Proc Natl Acad Sci USA 1987; 84:265-269.
12. Van Asperen J, Mayer U, van Tellingen O et al. The pharmacological role of P-glycoprotein in the blood-brain barrier. J Pharm Sci 1997; 86:881-884.
13. Tsuruo T, Iida H, Tsukagoshi S et al. Overcoming of vincristine resistance in P388 leukemia in vivo and in vitro through enhanced cytotoxicity of vincristine and vinblastine by verapamil. Cancer Res 1981; 41:1967-1972.
14. Ford J M, Hait W N. Pharmacology of drugs that alter multidrug resistance in cancer. Pharmacol Rev 1990; 42:155-199.
15. Slater L M, Sweet P, Stupecky M et al. Cyclosporin A reverses vincristine and daunorubicin resistance in acute lymphatic leukemia in vitro. J Clin Invest 1986; 77:1405-1408.
16. Hyafil F, Vergely C, Du Vignaud P et al. In vitro and in vivo reversal of multidrug resistance by GF120918, an acridonecarboxamide derivative. Cancer Res 1993; 53:4595-4602.
17. Van Zuylen L, Sparreboom A, Van der Gaast A et al. The orally administered P-glycoprotein inhibitor R101933 does not alter the plasma pharmacokinetics of docetaxel. Clin Cancer Res 2000; 6:1365-1371.
18. Dantzig A H, Shepard R L, Cao J et al. Reversal of P-glycoprotein-mediated multidrug resistance by a potent cyclopropyldibenzosuberane modulator, LY335979. Cancer Res 1996; 56:4171-4179.
19. Relling M V. Are the major effects of P-glycoprotein modulators due to altered pharmacokinetics of anticancer drugs? Ther Drug Monit 1996; 18:350-356.
20. Lum B L, Fisher G A, Brophy N A et al. Clinical trials of modulation of multidrug resistance: pharmacokinetic and pharmacodynamic considerations. Cancer 1993; 72(suppl 11): 3502-3514.
21. Dalton W S, Crowley J J, Salmon S S et al. A phase III randomized study of oral verapamil as a chemosensitizer to reverse drug resistance in patients with refractory myeloma: a Southwest Oncology Group Study. Cancer 1995; 75:815-820.
22. Milroy R. A randomised clinical study of verapamil in addition to combination chemotherapy in small cell lung cancer. West of Scotland Lung Cancer research Group and the Aberdeen Oncology Group. Br J Cancer 1993; 68:813-818.

23. Wishart G C, Bissett D, Paul J et al. Quinidine as a resistance modulator of epirubicin in advanced breast cancer: mature results of a placebo controlled randomized trial. J Clin Oncol 1994; 12:1771-1777.
24. Wacher V J, Wu C Y, Benet L Z. Overlapping substrate specificities and tissue distribution of cytochrome P450 3A and P-glycoprotein: implications for drug delivery and activity in cancer chemotherapy. Mol Carcinog 1995; 13:129-134.
25. Watkins P B. The barrier function of CYP3A4 and P-glycoprotein in the small bowel. Adv Drug Deliv Rev 1997; 27:161-170.
26. Wacher V J, Silverman J A, Zhang Y et al. Role of P-glycoprotein and cytochrome P450 3A in limiting oral absorption of peptides and peptidomimetics. J Pharm Sci 1998; 87:1322-1330.
27. Cummins C L, Jacobsen W, Benet L Z. Unmasking the dynamic interplay between intestinal P-glycoprotein and CYP3A4. J Pharmacol Exp Ther 2002; 300:1036-1045.
28. De Bruin M, Miyake K, Litman K et al. Reversal of resistance by GF120918 in cell lines expressing the half transporter, MXR. Cancer Lett 1999; 146:117-126.
29. Maliepaard M, van Gastelen M A, Tohgo A et al. Circumvention of BCRP-mediated resistance to camptothecins in vitro using non-substrate drugs or the BCRP inhibitor GF120918. Clin Cancer Res 2001; 7:935-941.
30. Guengerich F P. In vitro techniques for studying drug metabolism. J Pharmacokinet Biopharm 1998; 24:521-533.
31. Lin J H, Lu A Y. Inhibition and induction of cytochrome P450 and the clinical implications. Clin Pharmacokinet 1998; 35:361-390.
32. Watkins P B, Wrighton S A, Schuetz E G et al. Identification of glucocorticoid-inducible cytochromes P450 in the intestinal mucosa of rats and man. J Clin Invest 1987; 80:1029-1036.
33. Lown K S, Kolars J C, Thummel K E. Interpatient heterogeneity in expression of CYP3A4 and CYP3A5 in small bowel. Lack of prediction by the erythromycin breath test. Drug Metab Dispos 1994; 22:947-955.
34. Huizing M T, Misser V H, Pieters R C et al. Taxanes: a new class of antitumor agents. Cancer Invest 1995; 13:381-404.
35. Fujita H, Okamoto M, Takao A et al. Pharmacokinetics of paclitaxel in experimental animals. Part 1. Blood levels. Gan To Kagaku Ryoho 1994; 21:653-658.
36. Eiseman J L, Eddington N D, Leslie J et al. Plasma pharmacokinetics and tissue distribution of paclitaxel in CD2F1 mice. Cancer Chemother Phamacol 1994; 34:465-471.
37. Rowinsky E K, Wright M, Monsarrat B et al. Clinical pharmacology and metabolism of taxol (paclitaxel): update 1993. Ann Oncol 1994; 5(suppl 6):S7-S16.
38. Sonnichsen D S, Liu Q, Schuetz E G et al. Variability in human cytochrome P450 paclitaxel metabolism. J Pharmacol Exp Ther 1995; 275:566-575.
39. Walle T, Walle K, Kumar G N et al. Taxol metabolism and disposition in cancer patients. Drug Metabol Dispos 1995; 23:506-512.
40. Sparreboom A, van Tellingen O, Nooijen W J et al. Preclinical pharmacokinetics of paclitaxel and docetaxel. Anticancer Drugs 1998; 1:1-17.
41. Van Asperen J, van Tellingen O, Sparreboom A et al. Enhanced oral bioavailability of paclitaxel in mice treated with the P-glycoprotein blocker SDZ PSC 833. Br J Cancer 1997; 76:1181-1183.
42. Van Asperen J, van Tellingen O, van der Valk M A et al. Enhanced oral absorption and decreased elimination of paclitaxel in mice with cyclosporin A. Clin Cancer Res 1998; 4:2293-2297.
43. Harris J W, Rahman A, Kim B R et al. Metabolism of taxol by human hepatic microsomes and liver slices: participation of cytochrome P450 3A4 and an unknown P450 enzyme. Cancer Res 1994; 54:4026-4035.
44. Cresteil T, Monsarrat B, Alvinerie P et al. Taxol metabolism by human liver microsomes: identification of cytochrome P450 isozymes involved in its biotransformation. Cancer Res 1994; 54:386-392.
45. Webber I R, Peters W H, Back D J. Cyclosporin metabolism by human gastrointestinal mucosal microsomes. Br J Clin Pharmacol 1992; 33:661-664.
46. Bardelmeijer H A, Beijnen J H, Brouwer K R et al. Increased oral bioavailability of paclitaxel by GF120918 in mice through selective modulation of P-glycoprotein. Clin Cancer Res 2000; 6:4416-4421.
47. Wils P, Phung-Ba V, Warnery A et al. Polarized transport of docetaxel and vinblastine mediated by P-glycoprotein in human intestinal epithelial cell monolayers. Biochem Parmacol 1994; 48:1528-1530.
48. Shirakawa K, Takar K, Tanigawara Y et al. Interaction of docetaxel (Taxotere) with human P-glycoprotein. Jpn J Cancer Res 1999; 90:1380-1386.
49. Bardelmeijer H A, Ouwehand M, Buckle T et al. Low systemic exposure of oral docetaxel in mice resulting from extensive first-pass metabolism is boosted by ritonavir. Proc Am Assoc Cancer Res 2002; 43:262 and Cancer Research 2002; 62:6158-6164.
50. Marre F, Sanderink G J, Desousa G et al. Hepatic biotransformation of docetaxel (taxotere) in vitro: involvement of the CYP3A subfamily in humans. Cancer Res 1996; 56:1296-1302.
51. Meerum Terwogt J M, Malingré M M, Beijnen J H et al. Coadministration of cyclosporin enables oral therapy with paclitaxel. Clin Cancer Res 1999; 5:3379-3384.
52. Malingré M M, Terwogt J M, Beijnen J H et al. A phase I and pharmacokinetic study of oral paclitaxel. J Clin Oncol 2000; 18:2468-2475.
53. Malingré M M, Schellens J H M, van Tellingen O et al. Metabolism and excretion of paclitaxel after oral administration in combination with cyclosporin A and after intravenous administration. Anticancer Drugs 2000; 11:813-820.
54. Gianni L, Kearns C M, Giani A et al. Nonlinear pharmacokinetics and metabolism of paclitaxel and its pharmacokinetic/pharmacodynamic relationship in humans. J Clin Oncol 1995; 13:180-190.
55. Sparreboom A, van Tellingen O, Nooijen W J et al. Tissue distribution, metabolism and excretion of paclitaxel in mice. Anticancer Drugs 1996; 7:78-86.
56. van Tellingen O, Huizing M T, Panday V R et al. Cremophor EL causes (pseudo) nonlinear pharmacokinetics of paclitaxel in patients. Br J Cancer 1999; 81:330-335.
57. Malingré M M, Beijnen J H, Rosing H et al. A phase I and pharmacokinetic study of bidaily dosing of oral paclitaxel in combination with cyclosporin A. Cancer Chemother Pharmacol 2001; 47:347-354.
58. Malingré M M, Beijnen J H, Rosing H et al. The effect of different doses of cyclosporin A on the systemic exposure of orally administered paclitaxel. Anticancer Drugs 2001; 12:351-358.

59. Malingré M M, Beijnen J H, Rosing H et al. Co-administration of GF120918 significantly increases the systemic exposure to oral paclitaxel in cancer patients. Br J Cancer 2001; 84:42-47.
60. Kruijtzer C M F, Schellens J H M, Mezger J et al. A phase II and pharmacological study of weekly oral paclitaxel (Paxoral®) plus cyclosporin A (CsA) in patients with advanced non-small cell lung cancer (NSCLC). J Clin Oncol 2002; 20:4508-4516.
61. Wozniak A J. Single agent vinorelbine in the treatment of non-small cell lung cancer. Semin Oncol 1999; 26(suppl 16):62-66.
62. Ten Bokkel Huinink W W, Bergman B, Chemaissaini A et al. Single-agent gemcitabine: an active and better tolerated alternative to standard cisplatin-based therapy in locally advanced or metastatic non-small cell lung cancer. Lung Cancer 1999; 26:85-94.
63. Socinski M A. Single-agent paclitaxel in the treatment of advanced non-small cell lung cancer. The Oncologist 1999; 4:408-416.
64. Miller V, Kris M. Docetaxel (Taxotere) as a single agent and in combination chemotherapy for the treatment of patients with advanced non-small cell lung cancer. Semin Oncol 2000; 27(suppl 3):3-10.
65. Ranson M, Davidson N, Nicolson M et al. Randomized trial of paclitaxel plus supportive care versus supportive care for patients with advanced non-small cell lung cancer. J Natl Cancer Inst 2000; 92:1074-1080.
66. Gatzemeier U, Heckmayr M, Neuhauss R et al. Phase II study with paclitaxel for the treatment of advanced inoperable non-small cell lung cancer. Lung Cancer 1995; 12(suppl 2):S101-S106.
67. Cullinan S A, Moertel C G, Wieand H S et al. Controlled evaluation of three drug combination regimens versus fluorouracil alone for the therapy of advanced gastric cancer. J Clin Oncol 1994; 12:412-416.
68. Wils J A, Klein H O, Wagener D J et al. Sequential high-dose methotrexate and fluorouracil combined with doxorubicin. A step ahead in the treatment of advanced gastric cancer: a trial of the European Organization for Research and Treatment of Cancer Gastrointestinal Tract Cooperative Group. J Clin Oncol 1991; 9:827-831.
69. Webb A, Cunningham D, Scarffe H et al. Randomized trial comparing epirubicin, cisplatin, and fluorouracil versus fluorouracil, doxorubicin and methotrexate in advanced esophagogastric cancer. Clin Oncol 1997; 15:261-267.
70. Boot H, Cats A, Tonino S et al. Epirubicin, cisplatin and continuous 5-FU chemotherapy (ECF-regimen) in patients with cancer of the gastroesophageal junction and stomach. Gastroenterology 2002; 122(suppl):A601.
71. Ohtsu A, Boku N, Tamura F et al. An early phase II study of a 3-hour infusion of paclitaxel for advanced gastric cancer. Am J Clin Oncol 1998; 21:416-419.
72. Cascinu S, Graziano F, Cardarelli N et al. Phase II study of paclitaxel in pretreated advanced gastric cancer. Anticancer Drugs 1998; 9:307-310.
73. Einzig A L, Lipsitz S, Wiernik P H et al. Phase II trial of Taxol in patients with adenocarcinoma of upper gastrointestinal tract (UGIT). The Eastern Cooperative Oncology Group (ECOG) results. Invest New Drugs 1995; 3:223-227.
74. Huizing M T, Keung A C, Rosing H et al. Pharmacokinetics of paclitaxel and metabolites in a randomized comparative study in platinum pretreated ovarian cancer patients. J Clin Oncol 1993; 11:2127-2135.
75. Malingré M M, Richel D J, Beijnen J H et al. Coadministration of cyclosporin A strongly enhances the oral bioavailability of docetaxel. J Clin Oncol 2001; 19:1160-1166.
76. Burstein H J, Manola J, Younger J et al. Docetaxel administered on a weekly basis for metastatic breast cancer. J Clin Oncol 2000; 18:1212-1219.
77. Kruijtzer C M F, Malingré MM, Schornagel J H et al. A phase II study with weekly oral docetaxel and cyclosporin A in patients with metastatic breast cancer. Proc Am Soc Clin Oncol 2001; 20:1941.
78. Lück H J, Donnè S, Glaubitz M et al. Phase I study of weekly docetaxel (Taxotere®) in heavily pretreated breast cancer patients. Eur J Cancer 1997; 33(suppl): 158.
79. Hainsworth J D, Burris 3rd HA, Yardley D A et al. Weekly docetaxel in the treatment of elderly patients with advanced breast cancer: a Minnie Pearl Cancer Research Network Phase II trial. J Clin Oncol 2001; 19:3500-3505.
80. Bruno R, Hille D, Riva A et al. Population pharmacokinetics/pharmacodynamics of docetaxel in phase II studies in patients with cancer. J Clin Oncol 1998; 16:187-196.
81. Rosing H, Lustig V, van Warmerdam L J et al. Pharmacokinetics and metabolism of docetaxel administered as a 1-h intravenous infusion. Cancer Chemother Pharmacol 2000; 45:213-218.
82. Myers B D, Ross J, Newton L et al. Cyclosporine-associated chronic nephropathy. N Engl J Med 1984; 311:699-705.
83. Mastalerz H, Cook D, Fairchild C R, Hansel S, Johnson W, Kadow J F, Long B H, Rose W C, Tarrant J, Wu M J, Xue M Q, Zhang G, Zoeckler M, Vyas D M. The discovery of BMS-275183: an orally efficacious novel taxane. Bioorg Med Chem. 2003; 11:4315-23.
84. J. Collett, C. Moreton. Modified-release peroral dosage forms. In: M. E. Aulton, editor. Pharmaceutics: the science of dosage form design, 2nd edition. London: Churchill Livingstone, 2002: 289-305.
85. R Bruno and G. J. Sanderink, Pharmacokinetics and metabolism of Taxotere (docetaxel). Cancer Surv 17, 305-313 (1993).
86. W. J. Loos, S. D. Baker, J. Verweij, J. G. Boonstra and A. Sparreboom, Clinical pharmacokinetics of unbound docetaxel: role of polysorbate 80 and serum proteins. Clin Pharmacol Ther 74, 364-371 (2003).
87. B. S. Kappelhoff, A. D. R Huitema, K. M. L. Crommentuyn, J. W. Mulder, P. L. Meenhorst, E. C. van Gorp, A. T. Mairuhu and J. H. Beijnen, Development and validation of a population pharmacokinetic model for ritonavir used as a booster or as an antiviral agent in HIV-1-infected patients. Br J Clin Pharmacol 59, 174-182 (2005).
88. Martignoni M, Groothuis G M, de Kanter R. Species differences between mouse, rat, dog, monkey and human CYP-mediated drug metabolism, inhibition and induction. Expert Opin Drug Metab Toxicol. 2006 December; 2(6): 875-94
89. Xie W, Evans R M. Pharmaceutical use of mouse models humanized for the xenobiotic receptor. Drug Discov Today. 2002 May 1; 7(9):509-15.
90. Iyer M, Reschly E J, Krasowski M D. Functional evolution of the pregnane X receptor. Expert Opin Drug Metab Toxicol. 2006 June; 2(3):381-97.
91. Wang H, LeCluyse E L. Role of orphan nuclear receptors in the regulation of drug-metabolising enzymes. Clin Pharmacokinet. 2003; 42(15):1331-57.
92. Nelson D R, Zeldin D C, Hoffman S M, Maltais L J, Wain H M, Nebert D W. Comparison of cytochrome P450 (CYP) genes from the mouse and human genomes, including nomenclature recommendations for genes, pseudogenes and alternative-splice variants. Pharmacogenetics. 2004 January; 14(1):1-18.
93. Serajuddin A T. Solid dispersion of poorly water-soluble drugs: early promises, subsequent problems, and recent breakthroughs. J Pharm Sci 1999; 88(10): 1058 1066.
94. Karanth H, Shenoy V S, Murthy R R. Industrially feasible alternative approaches in the manufacture of solid dispersions: a technical report AAPS Pharm Sci Tech 2006; 7(4): 87.
95. Chen J, Qiu L, Hu M, Jin Y, Han J. Preparation, characterization and in vitro evaluation of solid dispersions containing docetaxel. Drug Development and Industrial Pharmacy 2008; 34:588-594.
96. Schellekens R C, Stuurman F E, van der Weert F H, Kosterink J G, Frijlink H W. A novel dissolution method relevant to intestinal release behaviour and its application in the evaluation of modified release mesalazine products. Eur. J. Pharm. Sci. 2007 January; 30(1): 15-20.
97. Dressman J B, Reppas C. In vitro-in vivo correlations for lipophilic, poorly water-soluble drugs. Eur. J. Pharm. Sci. 2000 October; 11: S73-S80.
98. The Handbook of Pharmaceutical Excipients. Fifth Edition. Edited by Raymond Rowe, Paul Sheskey and Sian Owen. See section on Povidone.
99. Kruijtzer C M, Boot H, Beijnen J H et al. Weekly oral paclitaxel as first line treatment in patients with advanced gastric cancer. Ann Oncol 2003; 14:197-204.
100. Helgason H, Kruijtzer C M, Huitema A D R et al. Phase II and pharmacological study of oral paclitaxel (Paxoral) plus ciclosporin in anthracycline-pretreated metastatic breast cancer. Brit J Cancer 2006; 95:794-800.
101. Kuppens I E, Van Maanen M J, Rosing H, Schellens J H M, Beijnen J H. Quantitative analysis of docetaxel in human plasma using liquid chromatography coupled with tandem mass spectrometry. Biomed Chromatogr 2005; 19:355-361.

The invention claimed is:

1. A solid pharmaceutical composition for oral administration comprising a substantially amorphous taxane, a hydrophilic carrier, and a surfactant, wherein the taxane is partly molecularly dispersed in the hydrophilic carrier, wherein the hydrophilic carrier is PVP-K30, wherein the surfactant is sodium dodecyl sulphate, wherein the taxane to hydrophilic carrier weight ratio is about 1:9 w/w, and wherein the weight ratio of surfactant to taxane is about 1:1 w/w.

2. The composition of claim 1 wherein the taxane is selected from docetaxel, paclitaxel, BMS-275183, functional derivatives thereof and pharmaceutically acceptable salts or esters thereof.

3. The composition of claim 1 wherein the taxane is selected from docetaxel, paclitaxel, functional derivatives thereof and pharmaceutically acceptable salts or esters thereof.

4. The composition of claim 1, further comprising one or more additional pharmaceutically active ingredients.

5. The composition of claim 4 wherein one or more of the additional pharmaceutically active ingredients is a CYP3A4 inhibitor.

6. The composition of claim 5 wherein the CYP3A4 inhibitor is ritonavir.

7. A method of treatment of a neoplastic disease, the method comprising the administration, to a subject in need of such treatment, of an effective amount of the composition according to claim 1.

8. A method of preparing a composition according to claim 1, comprising the steps of:
dissolving the taxane, the hydrophilic carrier, and the surfactant in a solvent; and
evaporating the solvent to form the composition.

9. A method of treating a neoplastic disease in a subject receiving a CYP3A4 inhibitor, comprising administering to the subject simultaneously, separately, or sequentially a composition according to claim 1.

10. The composition of claim 1, wherein the taxane is docetaxel.

11. The composition of claim 1, wherein the taxane is paclitaxel.

12. The composition of claim 1, which is prepared by solvent evaporation.

* * * * *